(12) United States Patent
Cheng

(10) Patent No.: US 12,154,777 B2
(45) Date of Patent: Nov. 26, 2024

(54) SYSTEMS AND METHODS FOR SINGLE PARTICLE ANALYSIS

(71) Applicant: Shanghai Polaris Biology Co., Ltd., Shanghai (CN)

(72) Inventor: Yupeng Cheng, Shanghai (CN)

(73) Assignee: SHANGHAI POLARIS BIOLOGY CO., LTD., Shanghai (CN)

( * ) Notice: Subject to any disclaimer, the term of this patent is extended or adjusted under 35 U.S.C. 154(b) by 397 days.

(21) Appl. No.: 17/523,654

(22) Filed: Nov. 10, 2021

(65) Prior Publication Data

US 2022/0148871 A1 May 12, 2022

Related U.S. Application Data

(63) Continuation of application No. PCT/CN2020/090016, filed on May 13, 2020.

(30) Foreign Application Priority Data

Jun. 14, 2019 (WO) ................ PCT/CN2019/091215

(51) Int. Cl.
*H01J 49/10* (2006.01)
*H01J 49/00* (2006.01)
(Continued)

(52) U.S. Cl.
CPC ........ *H01J 49/105* (2013.01); *H01J 49/0031* (2013.01); *H01J 49/063* (2013.01);
(Continued)

(58) Field of Classification Search
CPC .... H01J 49/105; H01J 49/0031; H01J 49/063; H01J 49/067; H01J 49/24; H01J 49/40;
(Continued)

(56) References Cited

U.S. PATENT DOCUMENTS

| | | | |
|---|---|---|---|
| 5,689,111 A | 11/1997 | Dresch et al. | |
| 5,763,878 A | 6/1998 | Franzen | |

(Continued)

FOREIGN PATENT DOCUMENTS

| | | | |
|---|---|---|---|
| CA | 2447057 A1 | 5/2004 | |
| CA | 2463433 C | 6/2012 | |

(Continued)

OTHER PUBLICATIONS

Bandura et al., Mass cytometry: technique for real time single cell multitarget immunoassay based on inductively coupled plasma time-of-flight mass spectrometry. Analytical Chemistry 81: 6813-6822 (2009).

(Continued)

*Primary Examiner* — Kiet T Nguyen
(74) *Attorney, Agent, or Firm* — WILSON SONSINI GOODRICH & ROSATI

(57) ABSTRACT

Systems and methods are provided for the analysis of single particles with inductively coupled plasma time of flight mass spectrometry. Single particles may be isolated from whole cells, microorganisms, viruses, etc. The systems may include curved ion guides including such elements as multipoles, angled or rounded surfaces, and an ion manipulation device including elements such as an ion tunnel, ion funnel, quadrupole, and variations of each element.

16 Claims, 23 Drawing Sheets

(51) Int. Cl.
  *H01J 49/06* (2006.01)
  *H01J 49/24* (2006.01)
  *H01J 49/40* (2006.01)

(52) U.S. Cl.
  CPC ............ *H01J 49/067* (2013.01); *H01J 49/24* (2013.01); *H01J 49/40* (2013.01)

(58) Field of Classification Search
  CPC ....... G01N 15/1031; G01N 2015/1006; G01N 33/6848; G01N 2458/15
  USPC .................................................. 250/281, 282
  See application file for complete search history.

(56) References Cited

U.S. PATENT DOCUMENTS

| | | |
|---|---|---|
| 6,265,717 B1 | 7/2001 | Sakata et al. |
| 6,586,730 B1 | 7/2003 | Kamimura et al. |
| 6,777,671 B2 | 8/2004 | Doroshenko et al. |
| 6,838,662 B2 | 1/2005 | Bateman et al. |
| 6,891,157 B2 | 5/2005 | Bateman et al. |
| 6,900,431 B2 | 5/2005 | Belov et al. |
| 6,987,264 B1 | 1/2006 | Whitehouse et al. |
| 7,034,287 B2 | 4/2006 | Okumura et al. |
| 7,034,292 B1 | 4/2006 | Whitehouse et al. |
| 7,196,326 B2 | 3/2007 | Franzen et al. |
| 7,326,925 B2 | 2/2008 | Verentchikov et al. |
| 7,365,317 B2 | 4/2008 | Whitehouse et al. |
| 7,459,693 B2 | 12/2008 | Park et al. |
| 7,495,212 B2 | 2/2009 | Kim et al. |
| 7,514,673 B2 | 4/2009 | Senko et al. |
| 7,781,728 B2 | 8/2010 | Senko et al. |
| 7,829,841 B2 | 11/2010 | Bateman et al. |
| 7,838,826 B1 | 11/2010 | Park et al. |
| 7,851,752 B2 | 12/2010 | Kim et al. |
| 7,919,747 B2 | 4/2011 | Green et al. |
| 8,222,597 B2 | 7/2012 | Kim et al. |
| 8,299,422 B2 | 10/2012 | Bateman et al. |
| 8,309,936 B2 | 11/2012 | Kreckel et al. |
| 8,324,565 B2 | 12/2012 | Mordehai et al. |
| 8,455,819 B2 | 6/2013 | Green et al. |
| 8,525,107 B2 | 9/2013 | Bandura et al. |
| 8,569,687 B2 | 10/2013 | Bateman et al. |
| 8,586,917 B2 | 11/2013 | Green et al. |
| 8,679,858 B2 | 3/2014 | Nolan et al. |
| 8,680,462 B2 | 3/2014 | Zanon et al. |
| 8,723,107 B2 | 5/2014 | Whitehouse et al. |
| 8,735,805 B2 | 5/2014 | Bateman et al. |
| 9,006,646 B2 | 4/2015 | Kalinitchenko |
| 9,048,073 B2 | 6/2015 | Bateman et al. |
| 9,123,516 B2 | 9/2015 | Hasegawa et al. |
| 9,123,518 B2 | 9/2015 | Giles et al. |
| 9,184,039 B2 | 11/2015 | Pringle et al. |
| 9,269,549 B2 | 2/2016 | Green et al. |
| 9,410,927 B2 | 8/2016 | Bateman et al. |
| 9,564,305 B2 | 2/2017 | Berkout et al. |
| 9,786,479 B2 | 10/2017 | Green et al. |
| 9,799,503 B2 | 10/2017 | Williams et al. |
| 9,952,134 B2 | 4/2018 | Bandura et al. |
| 10,109,471 B1 | 10/2018 | Berkout et al. |
| 10,163,614 B1 | 12/2018 | Hall et al. |
| 2004/0195503 A1 | 10/2004 | Kim et al. |
| 2004/0211897 A1 | 10/2004 | Kim et al. |
| 2005/0218319 A1 | 10/2005 | Bandura et al. |
| 2009/0314934 A1* | 12/2009 | Brown .................. H01J 49/408 250/281 |
| 2011/0121170 A1 | 5/2011 | Park |
| 2011/0168880 A1 | 7/2011 | Ristroph et al. |
| 2012/0298853 A1 | 11/2012 | Kurulugama et al. |
| 2013/0068942 A1 | 3/2013 | Verenchikov et al. |
| 2014/0353484 A1* | 12/2014 | Tanner .................. H01J 49/40 250/282 |
| 2015/0233866 A1* | 8/2015 | Verenchikov ........ G01N 27/623 250/282 |
| 2017/0089862 A1 | 3/2017 | Bateman et al. |
| 2018/0374693 A1 | 12/2018 | Hall et al. |
| 2019/0164737 A1* | 5/2019 | Gillig .................... H01J 49/063 |

FOREIGN PATENT DOCUMENTS

| | | |
|---|---|---|
| CA | 2823790 A1 | 8/2012 |
| CA | 2687222 C | 7/2013 |
| CA | 2747956 C | 1/2014 |
| CA | 2626209 C | 1/2016 |
| CA | 2955865 A1 | 2/2016 |
| CA | 2585565 C | 9/2016 |
| CA | 2861514 C | 10/2016 |
| CA | 2650390 C | 5/2017 |
| CN | 101915800 A | 12/2010 |
| CN | 101305444 B | 3/2011 |
| CN | 101479828 B | 11/2011 |
| CN | 101681786 B | 6/2012 |
| CN | 104067116 A | 9/2014 |
| CN | 103250229 B | 4/2016 |
| CN | 103329242 B | 10/2016 |
| CN | 106373854 A | 2/2017 |
| CN | 106575599 A | 4/2017 |
| CN | 107037118 A | 8/2017 |
| CN | 105470096 B | 6/2018 |
| CN | 108987238 A | 12/2018 |
| CN | 109003877 A | 12/2018 |
| CN | 105810550 B | 10/2019 |
| DE | 20320484 U1 | 9/2004 |
| DE | 10350664 B4 | 10/2008 |
| DE | 602004010737 T2 | 12/2008 |
| EP | 1467397 B1 | 12/2007 |
| EP | 2160751 B1 | 12/2014 |
| EP | 1810314 B1 | 4/2015 |
| EP | 2913840 A1 | 9/2015 |
| EP | 2668660 A4 | 12/2015 |
| EP | 3048636 A1 | 7/2016 |
| EP | 1465234 B1 | 11/2016 |
| EP | 1943663 B1 | 1/2018 |
| EP | 3175474 A4 | 3/2018 |
| EP | 2013895 B1 | 9/2018 |
| EP | 2013895 B8 | 7/2019 |
| EP | 2626888 B1 | 7/2019 |
| EP | 3550587 A1 | 10/2019 |
| EP | 3550588 A1 | 10/2019 |
| EP | 3550589 A1 | 10/2019 |
| GB | 2396958 B | 11/2004 |
| GB | 2403591 B | 9/2005 |
| GB | 2421840 B | 11/2007 |
| GB | 2434249 B | 6/2010 |
| GB | 2455593 B | 11/2010 |
| GB | 2437829 B | 12/2010 |
| JP | 2004259452 A | 9/2004 |
| JP | 2009516842 A | 4/2009 |
| JP | 4778560 B2 | 9/2011 |
| JP | 4913066 B2 | 4/2012 |
| JP | 5290960 B2 | 9/2013 |
| JP | 5334334 B2 | 11/2013 |
| JP | 2014504784 A | 2/2014 |
| JP | 5686566 B2 | 3/2015 |
| JP | 6577017 B2 | 9/2019 |
| KR | 20170042300 A | 4/2017 |
| MX | 2017001307 A | 5/2017 |
| RU | 2698795 C2 | 8/2019 |
| WO | WO-03060945 A1 | 7/2003 |
| WO | WO-2006048642 A2 | 5/2006 |
| WO | WO-2007052025 A2 | 5/2007 |
| WO | WO-2007125354 A2 | 11/2007 |
| WO | WO-2008157019 A2 | 12/2008 |
| WO | WO-2010041296 A1 | 4/2010 |
| WO | WO-2012046430 A1 | 4/2012 |
| WO | WO-2012100299 A1 | 8/2012 |
| WO | WO-2015122920 A1 | 8/2015 |
| WO | WO-2016018990 A1 | 2/2016 |
| WO | WO-2017013832 A1 | 1/2017 |
| WO | WO-2019193170 A1 | 10/2019 |
| WO | WO-2019193171 A1 | 10/2019 |

(56) References Cited

FOREIGN PATENT DOCUMENTS

| WO | WO-2019193191 A1 | 10/2019 |
|----|------------------|---------|
| WO | WO-2020248757 A1 | 12/2020 |
| WO | WO-2021142651 A1 | 7/2021 |

OTHER PUBLICATIONS

Baranov, et al. The potential for elemental analysis in biotechnology. Journal of Analytical Atomic Spectrometry. 2002. 17(9):1148-1152. Doi: 10.1039/B201494G.

Bjornson et al., Single-cell mass cytometry for analysis of immune system functional states. Current Opinion in Immunology 25: 484-494 (2013).

He, et al. Development of a capillary high-performance liquid chromatography tandem mass spectrometry system using SWIFT technology in an ion trap/reflectron time-of-flight mass spectrometer. Rapid Commun Mass Spectrom. 1997;11(16):1739-1748. doi:10.1002/(SICI)1097-0231(19971030)11:16<1739::AID-RCM773.0.CO;2-3.

Heddle, D W O. An afocal electrostatic lens. Journal of Physics E: Scientific Instruments. vol. 4. Number 12. 1971. pp. 981-983.

Julian, et al. Broad-band excitation in the quadrupole ion trap mass spectrometer using shaped pulses created with the inverse Fourier transform. Analytical Chemistry. 1993. 65 (14). pp. 1827-1833. DOI: 10.1021/ac00062a006.

Julian, et al. Ion funnels for the masses: experiments and simulations with a simplified ion funnel. J Am Soc Mass Spectrom. Oct. 2005; 16(10):1708-12. doi: 10.1016/j.jasms.2005.06.012.

Kelly, et al. The ion funnel: theory, implementations, and applications. Mass spectrometry reviews 29.2 (Apr. 23, 2009): 294-312.

Kim, et al. Design and implementation of a new electrodynamic ion funnel. Analytical Chemistry. May 15, 2000. 72(10):2247-55. DOI: 10.1021/AC991412X.

Mamyrin, et al. The mass-reflectron, a new nonmagnetic time-of-flight mass spectrometer with high resolution. Sov. Phys. JETP. vol. 37 No. 1. Jul. 1973. pp. 45-48.

PCT/CN2020/090016 International Search Report with Written Opinion dated Aug. 12, 2020.

Quinn, et al. Simultaneous determination of proteins using an element-tagged immunoassay coupled with ICP-MS detection. Journal of Analytical Atomic Spectrometry. 2002. 17. pp. 892-896. DOI: 10.1039/b202306g.

Shaffer, et al. An ion funnel interface for improved ion focusing and sensitivity using electrospray ionization mass spectrometry. Analytical Chemistry. Oct. 1, 1998;70(19):4111-9. DOI: 10.1021/ac9802170.

Sise, O., Electrostatic afocal-zoom lens design using computer optimization technique. Journal of Electron Spectroscopy and Related Phenomena. 197 (2014) pp. 7-12. DOI: 10.1016/j.elspec.2014.07.014.

Song, et al. Mass selection of ions from beams using waveform isolation in radiofrequency quadrupoles. Analytical chemistry 81.5 (2009): 1833-1840.

Zhang, et al. A novel combination of immunoreaction and ICP-MS as a hyphenated technique for the determination of thyroid-stimulating hormone (TSH) in human serum. Dec. 2001. Journal of Analytical Atomic Spectrometry. 16(12):1393-1396. DOI: 10.1039/B106387C.

Zhang, et al. ICP-MS-based competitive immunoassay for the determination of total thyroxin in human serum. Journal of Analytical Atomic Spectrometry. 2002. 17(10):1304-1307. DOI: 10.1039/b205623b.

\* cited by examiner

High pass quadrupole device with only RF voltage applied
a)

Band pass quadrupole device with both RF and DC voltage applied
b)

c)

d)

e)

SYSTEMS AND METHODS FOR SINGLE PARTICLE ANALYSIS

CROSS-REFERENCE

This application is a continuation application of International Application No. PCT/CN2020/090016 filed on May 13, 2020, which claims priority from PCT Application No. PCT/CN2019/091215 which was filed on Jun. 14, 2019, the content of which is hereby incorporated by reference in its entirety.

BACKGROUND OF THE INVENTION

Many single biological particles, such as cells, microorganisms, viruses and so on, have very complicate compositions and functions. For obtaining better results of functional and phenotypical identification, it is usually required to perform quantitative analysis of multi-parameters simultaneously.

Traditional flow cytometer is used for qualitative and quantitative analysis of single cells. It can meet the above requirement to some extent. However, due to the limitation of available fluorochromes, so far, the analysis for single cells based on flow cytometer can only simultaneously detect parameters of less than 20.

Mass cytometry is a new technology recently developed for simultaneous multi-parameter analysis of single cells. It is different from flow cytometer, metal isotopes instead of fluorochromes are used to bind with specific antibodies. The antibodies tagged with metal isotopes are used to bind with corresponding antigens of cells through the antigen-antibody reaction, which is usually called 'staining'. The stained cells are analyzed by ICP-TOF MS to obtain the information of metal isotopes, according to which the information of antigens can also be derived. Theoretically, over 100 antigens can be simultaneously detected in single cell, since there are many available elements in periodical table of elements. For avoiding the interference of naturally existed elements in cells and environment, lanthanide elements are usually used.

In all of the current mass spectrometers, ICP-TOF MS is the best choice for simultaneous multi-parameter analysis of single cells. It is mainly due to the excellent atomization and ionization performance of ICP. The sample introduced into ICP can be atomized and ionized as much as possible, which produces very high ionization efficiency. TOF is a very fast and multi-channel mass analyzer, which is quite suitable for transient signal detection.

In the invention, an instrument and related method based on ICP-TOF MS are disclosed for analysis of single particles including cells, microorganisms, viruses and so on, tagged with metal isotopes. The instrument comprises sample introduction device, ICP ionization device, atmospheric pressure interface, ion guide device, ion manipulation device, TOF mass analyzer, ion detector and signal processing device.

Sample introduction device is used to transport single particles tagged with metal isotopes into ICP ionization device, where they will be evaporated, atomized and ionized to finally generate ions of metal isotopes. The ions get into vacuum through atmospheric pressure interface and are transported by ion guide device into downstream ion manipulation device. Ions are further processed in ion manipulation device for improving the performance, such as duty cycle, of TOF mass analyzer. Ions are separated in the TOF mass analyzer and arrive at the ion detector sequentially. The ion signal generated from the ion detector is processed by the signal processing device to form as mass spectrum.

While ions enter into the vacuum, lots of neutral gas molecules are also together with them. These neutral gas molecules do not only decrease signal noise ratio of instrument, but also increase the burden of next stage vacuum pump. In the invention, an off-axis ion guide device is disclosed to transport ions effectively and remove neutral gas molecules. At the same time, it can also compress ion beam radially to further increase the ion transmission efficiency. In addition, the advantage of off-axis ion guide device includes high flexibility of instrument layout design and smaller instrument footprint.

Argon gas is used as working gas in the ICP ionization device, therefore many ions related with Argon, including $Ar+$, $ArCl+$, $ArC+$, $ArAr+$, $ArN+$, $ArNa+$ and so on, will be formed. Except of these, there are also lots of $C+$, $N+$, $O+$ and other ions. Usually, these ions without any relationship with targeted ions, metal isotopes, are called interference ions or noise ions. The abundance of these interference ions is so high that it is even much higher than that of targeted ions. On one hand, their masses may be very similar with that of targeted ions, which will affect the accuracy of qualitative and quantitative results. On the other hand, these interference ions will generate extremely serious space charge effect, which decreases ion transmission a lot and bring lower sensitivity. Especially for the case of weak ion signal, the problem of space charge will affect the detection of limit of instrument and reproducibility. In the analysis of single cells, the quantities of different antigens may vary a lot, these high abundant interference ions will limit the dynamic range. In the invention, a novel ion manipulation device is disclosed for selectively filtering ions with arbitrary mass. Without affecting the ion transmission of targeted ions, it can remove the interference ions effectively and reduce the space charge effect. At the same time, it also avoids the continuous bombardment of high abundant interference ions to ion detector, which increases the lifetime of ion detector significantly.

Orthogonal acceleration time-of-flight is a pulsed mass analyzer. While ions fly into the orthogonal acceleration region of TOF mass analyzer, they will be accelerated by a pulsed acceleration voltage. Ions with different masses obtained same kinetic energy but different velocity. The flight of time for them is different after travelling out same flight path. According to their flight of time, the corresponding information of mass can be deduced. Usually, during the first pulse of ions is flying in the TOF mass analyzer, the following ions will also be filled into the orthogonal acceleration region for preparation of next pulse. However, there is no any ion storage device in the orthogonal acceleration region, so most of ions continuously fly into the orthogonal acceleration region will be lost. Generally, the ratio of accelerated ions to total ions is called duty cycle. For the traditional orthogonal acceleration TOF mass analyzer, the typical duty cycle is only 5%~30%. The lower the duty cycle, the fewer the detected ions. In the invention, a novel ion manipulation device is disclosed for ion bunching and accumulation. It can divide the continuous ion flow into separated ion groups and adjust the interval time between adjacent ion groups to synchronize with the pulse frequency of acceleration voltage. Therefore, the duty cycle can be improved a lot.

Ion manipulation devices presently available comprise flat surfaces which are limited with regard to their ability to store ions by ion bunching or accumulation. Additionally, such flat surfaces are inefficient at filtering out interference ions or noise ions. With complex samples such as cells, there is a need for ion manipulation devices with enhanced ion bunching and accumulation capabilities as well as a higher efficiency in filtering out interference ions or noise ions.

SUMMARY OF THE INVENTION

Disclosed herein is an instrument and related methods based on ICP-TOF MS designed to analyze single particles tagged with metal isotopes. Single particles can be isolated from whole cells, microorganisms, viruses, etc. In one embodiment, the instrument comprises a sample introduction device, an ICP ionization device, an atmospheric pressure device, an ion guide device, and ion manipulation device, a TOF mass analyzer, an ion detector, and a signal processing device.

Disclosed herein is an inductively-coupled plasma time-of-flight mass spectrometer for analysis of single particles tagged with metal isotopes, said mass spectrometer comprising a sample introduction device configured to sequentially generate the single particles, an ionization device for generating ions of the metal isotopes from the single particles received through the sample introduction device, an atmospheric pressure interface for transport of the ions with aid of a vacuum, an ion guide arrangement configured to receive the ions from the atmospheric pressure interface and transport the ions, an ion manipulation device configured to receive the ions from the ion guide device and configured to perform one or more of (1) selectively filtering ions with specific masses, (2) providing ion bunching, and (3) providing ion storage, a time-of flight (TOF) mass analyzer configured to receive the ions and separate ions with different masses to arrive at an ion detector at different times, and a signal processing device configured to process an ion flow signal from the ion detector and form a mass spectrum for identification of the metal isotopes.

Disclosed herein is a method for analyzing single particles tagged with metal isotopes via an inductively-coupled plasma time-of-flight mass spectrometer, said method comprising sequentially generating the single particles via a sample introduction device, generating, with aid of an ionization device, ions of the metal isotopes from the single particles received through the sample introduction device, transporting, using an atmospheric pressure interface, the ions with aid of a vacuum, receiving, via an ion guide arrangement, the ions from the atmospheric pressure interface, and transporting the ions, receiving, via an ion manipulation device, the ions from the ion guide device, and performing one or more of (1) selectively filtering ions with specific masses, (2) providing ion bunching, and (3) providing ion storage, separating, via a time-of flight (TOF) mass analyzer, the ions with different masses to arrive at an ion detector at different times, and processing, via a signal processing device, an ion flow signal from the ion detector and form a mass spectrum for identification of the metal isotopes. The single particles can be single cells, biological molecules, or polymer microspheres. The sample introduction device can be configured to sequentially generate the single particles tagged with metal isotopes. The ionization device can be an inductively coupled plasma ionization device. The ionization device can be configured to evaporate, atomize, and ionize the single particles. The ionization device can be configured to generate monoatomic or polyatomic ions from the single particles. The ionization device can use microwave plasma torch (MPT), glow discharge ionization (GDI), or laser ionization (LI). The atmospheric pressure interface can comprise two or more cone shaped components, these components can be perforated. The atmospheric pressure interface can comprise one or more adjacent vacuum chambers. A corresponding vacuum pump can be provided for each of the vacuum chambers.

The ion guide arrangement can utilize an electrostatic lens, a quadrupole arrangement, a multipole arrangement, an ion tunnel, and/or an ion funnel. The ion guide arrangement can have a curved shape. The ion guide arrangement can comprise a first curved electrode having a concave surface, wherein said concave surface comprises a first planar surface and a second planar surface that meets the first planar surface and is not parallel to the first planar surface; a second curved electrode having a convex surface, wherein said convex surface comprises a third planar surface and a fourth planar surface that meets the third planar surface and is not parallel to the fourth planar surface; and a gap between the first curved electrode and the second curved electrode configured to permit passage of targeted ions between the first curved electrode and the second curved electrode. The ion guide arrangement can comprise a first electrode comprising a curved section and one or more linear sections adjacent to the curved section; a second electrode comprising a curved section and one or more linear sections adjacent to the curved section; and a gap between the first electrode and the second electrode configured to permit passage of targeted ions between the first electrode and the second electrode.

Disclosed herein is an ion guide arrangement for use in an inductively coupled plasma time-of-flight mass spectrometer, said ion guide comprising a first curved electrode having a concave surface, wherein said concave surface comprises a first planar surface and a second planar surface that meets the first planar surface and is not parallel to the first planar surface, a second curved electrode having a convex surface, wherein said convex surface comprises a third planar surface and a fourth planar surface that meets the third planar surface and is not parallel to the fourth planar surface, and a gap between the first curved electrode and the second curved electrode configured to permit passage of targeted ions between the first curved electrode and the second curved electrode. The ion guide arrangement can be used for the analysis of a sample of single particles tagged with metal isotopes.

Further disclosed herein is a method for guiding targeted ions through an ion guide arrangement for use in an inductively coupled plasma time-of-flight mass spectrometer, said method comprising providing a first curved electrode having a concave surface, wherein said concave surface comprises a first planar surface and a second planar surface that meets the first planar surface and is not parallel to the first planar surface, and providing a second curved electrode having a convex surface, wherein said convex surface comprises a third planar surface and a fourth planar surface that meets the third planar surface and is not parallel to the fourth planar surface, wherein a gap is provided between the first curved electrode and the second curved electrode, and said gap is configured to permit passage of the targeted ions between the first curved electrode and the second curved electrode, wherein the first planar surface is parallel to the third planar surface, and wherein the second planar surface is parallel to the fourth planar surface. In one embodiment, the first planar surface is not parallel to the third planar surface, and the second planar surface is not parallel to the fourth planar surface. The concave surface of the first curved electrode may directly face the convex surface of the second curved electrode. A length of the concave surface of the first curved electrode may curve inwards. A length of the convex surface of the second curved electrode may curve outwards. A first voltage may be applied to the first curved electrode and a second voltage different from the first voltage may be applied to the second curved electrode. The ion guide arrangement may be configured to focus ions radially upon application of the first voltage and the second voltage. The passage of the targeted ions may occur along an axial direction along a length of the first curved electrode and the second curved electrode. The targeted ions may be from metal isotope ions for tagging single particles. The ion guide arrangement may be configured to guide ions around at least a 90 degree angle, at least a 180 degree angle. The ion guide arrangement may be configured to receive ions from an upstream perforated cone-shaped component. The ion guide arrangement may be configured to transport target ions to an ion manipulation device configured to further process the ions. The ion guide arrangement may be configured to receive ions from an ion manipulation device configured to process ions. The ion guide arrangement may be configured to transport target ions for subsequent access by a time-of-flight (TOF) mass analyzer.

Disclosed herein is an ion guide arrangement for use in an inductively coupled plasma time-of-flight mass spectrometer, said method comprising a first electrode comprising a curved section and one or more linear sections adjacent to the curved section, a second electrode comprising a curved section and one or more linear sections adjacent to the curved section, and a gap between the first electrode and the second electrode configured to permit passage of targeted ions between the first electrode and the second electrode. The ion guide arrangement can be applied to analyze a sample of single particles tagged with metal isotopes.

Disclosed herein is a method for guiding targeted ions through an ion guide arrangement for use in an inductively coupled plasma time-of-flight mass spectrometer, said method comprising providing a first voltage to a first electrode comprising a curved section and one or more linear sections adjacent to the curved section, and providing a second voltage to a second electrode comprising a curved section and one or more linear sections adjacent to the curved section, wherein a gap is provided between the first electrode and the second electrode, said gap configured to permit passage of targeted ions between the first electrode and the second electrode. One or more linear sections may be provided in direct contact with the curved section of the first electrode or the second electrode. The curved section of the first electrode or the second electrode may be positioned between at least two linear sections. The first electrode and the second electrode may comprise a same cross-sectional shape along a length of the first electrode and the second electrode including the curved section and the one or more linear sections. The first electrode may comprise a concave surface, wherein said concave surface comprises a first planar surface and a second planar surface that meets the first planar surface and is not parallel to the first planar surface. The concave surface may extend along the curved section of the first electrode and the one or more linear sections adjacent to the curved section. The second electrode may comprise a convex surface, wherein said convex surface comprises a third planar surface and a fourth planar surface that meets the third planar surface and is not parallel to the fourth planar surface. The concave surface may extend along the curved section of the second electrode and the one or more linear sections adjacent to the curved section. The concave surface of the first curved electrode may directly face the convex surface of the second curved electrode. A length of the concave surface of the first curved electrode may curve inwards. A length of the convex surface of the second curved electrode may curves outward. A first voltage may be applied to the first electrode and a second voltage different from the first voltage is applied to the second electrode. The ion guide arrangement may be configured to deflect and focus ions radially upon application of the first voltage and the second voltage. The passage of the targeted ions may occur along an axial direction along a length of the first electrode and the second electrode. The targeted ions may be metal isotope ions. The ion guide arrangement may be configured to guide ions around at least a 90 degree angle. The ion guide arrangement may be configured to guide ions around at least a 180 degree angle. The ion guide arrangement may be configured to receive ions from an upstream perforated cone-shaped component. The ion guide arrangement may be configured to transport target ions to an ion manipulation device configured to further process the ions. The ion guide arrangement may be configured to receive ions from an ion manipulation device configured to process ions. The ion guide arrangement may be configured to transport target ions for subsequent access by a time-of-flight (TOF) mass analyzer.

Disclosed herein is an ion guide arrangement for use in an inductively coupled plasma time-of-flight mass spectrometer, said ion guide comprising a first curved section comprising a first set of poles, wherein RF voltages with opposite polarities are superimposed on adjacent poles, a second curved section comprising a second set of poles, wherein RF voltages with opposite polarities as superimposed on adjacent poles, and a gap between the first curved section and the second curved section configured to permit passage of targeted ions between the first curved section and the second curved section, wherein a first voltage is applied to the first curved section and a second voltage different from the first voltage is applied to the second curved section.

Disclosed herein is a method for guiding targeted ions through an ion guide arrangement for use in an inductively coupled plasma time-of-flight mass spectrometer, said method comprising providing a first curved section comprising a first set of poles, wherein RF voltages with opposite polarities are superimposed on adjacent poles, and providing a second curved section comprising a second set of poles, wherein RF voltages with opposite polarities as superimposed on adjacent poles, wherein a gap is provided between the first curved section and the second curved section, said gap configured to permit passage of targeted ions between the first curved section and the second curved section, and wherein a first voltage is applied to the first curved section and a second voltage different from the first voltage is applied to the second curved section. The first set of poles may be arranged to form a concave profile, wherein said concave profile comprises a first planar segment and a second planar segment that meets the first planar segment and is not parallel to the first planar segment. The concave profile may extend along a length of the first curved section. The second set of poles may be arranged to form a convex profile, wherein said convex profile comprises a third planar segment and a fourth planar segment that meets the third planar segment and is not parallel to the third planar segment. The convex profile may extend along a length of the second curved section. The concave profile of the first curved section may directly face the convex profile of the second curved section. A length of the concave profile of the first curved section may curve inwards, and a length of the convex profile of the second curved section may curve outwards. A length of the concave profile of the first curved section may curve laterally, and a length of the convex profile of the second curved section may curve laterally in the same direction. The ion guide arrangement may be configured to focus ions radially upon application of the first voltage and the second voltage. The first set of poles and the second set of poles may have a circular cross-section or a quadrilateral cross-section. A distance between the first curved section and the second curved section may remain the same along a profile of the first curved section facing the second curved section and a profile of the second curved section facing the first curved section. The passage of the targeted ions may occur along an axial direction along a length of the first curved section and the second curved section. The targeted ions may be metal isotope ions. The ion guide arrangement may be configured to guide ions around at least a 90 degree angle. The ion guide arrangement may be configured to guide ions around at least a 180 degree angle. The ion guide arrangement may be configured to receive ions from an upstream perforated cone-shaped component. The ion guide arrangement may be configured to transport target ions to an ion manipulation device configured to further process the ions. The ion guide arrangement may be configured to receive ions from an ion manipulation device configured to process ions. The ion guide arrangement may be configured to transport target ions for subsequent access by a time-of-flight (TOF) mass analyzer.

Disclosed herein is an ion manipulation device for use in an inductively coupled plasma time-of-flight mass spectrometer, said ion manipulation device comprising a first set of poles arranged in a parallel manner with a space between the poles, a second set of poles arranged in a parallel manner and positioned in an alternating arrangement with respect to the first set of poles. Voltages applied to the first set of poles may include a stored-waved form inverse Fourier transform (SWIFT) voltage.

Disclosed herein is a method for manipulating targeted ions via an ion manipulation device for use in an inductively coupled plasma time-of-flight mass spectrometer, said method comprising providing a first set of poles arranged in a parallel manner with a space between the poles, providing a second set of poles arranged in a parallel manner and positioned in an alternating arrangement with respect to the first set of poles, and applying voltages to the first set of poles, said voltages include a stored-waved form inverse Fourier transform (SWIFT) voltage. The voltages applied to the first set of poles may include an RF voltage plus a SWIFT voltage. Voltages applied to the second set of poles may include a minus RF voltage. Voltages applied to the second set of poles may include a minus RF voltage minus a SWIFT voltage. A first voltage applied to a first pole within the first set of poles may include an RF voltage plus a SWIFT voltage and a second voltage applied to a second pole within the first set of poles includes an RF voltage minus a SWIFT voltage. Voltages applied to the second set of poles may include a minus RF voltage. The first set of poles may comprise a pair of poles, and the second set of poles may comprise a pair of poles. The targeted ions may be manipulated along an axial direction along a length of the first set of poles and the second set of poles. The targeted ions may be metal isotope ions. The ion manipulation device may be configured to receive ions that have passed through an upstream perforated cone-shaped component. The ion manipulation device may be configured to receive ions from an upstream ion guide arrangement. The ion manipulation device may be configured to transport target ions to an ion guide arrangement configured to further guide the ions. The ion manipulation device may be configured to transport target ions for subsequent access by a time-of-flight (TOF) mass analyzer.

Disclosed herein is an ion manipulation device for use in an inductively coupled plasma time-of-flight mass spectrometer, said ion manipulation device comprising a plurality of stacked ring electrodes forming a tunnel having an entrance at one end and an exit at another end, wherein RF voltages of opposite polarities are applied to adjacent ring electrodes, wherein DC voltages are applied separately to each ring electrode for controlling ion movement in an axial direction through the ring electrodes, and wherein an amplitude of the RF voltages applied to the ring electrodes is gradually increased and DC voltages are gradually decreased from the entrance to the exit.

Disclosed herein is a method for manipulating targeted ions via an ion manipulation device for use in an inductively coupled plasma time-of-flight mass spectrometer, said method comprising providing a plurality of stacked ring electrodes forming a tunnel having an entrance at one end and an exit at another end, applying RF voltages of opposite polarities to adjacent ring electrodes, and applying DC voltages separately to each ring electrode for controlling ion movement in an axial direction through the ring electrodes, wherein an amplitude of the RF voltages applied to the ring electrodes is gradually increased and DC voltages are gradually decreased from the entrance to the exit. An axial space between each of the ring electrodes may be substantially the same or may change along the length of the tunnel. A thickness of each of the ring electrodes may be substantially the same. A thickness of the ring electrodes may change along the length of the tunnel. The targeted ions may be manipulated along an axial direction through the plurality of stacked ring electrodes. The targeted ions may be metal isotope ions. The ion manipulation device may be configured to receive ions that have passed through an upstream perforated cone-shaped component. The ion manipulation device may be configured to receive ions from an upstream ion guide arrangement. The ion manipulation device may be configured to transport target ions to an ion guide arrangement configured to further guide the ions. The ion manipulation device may be configured to transport target ions for subsequent access by a time-of-flight (TOF) mass analyzer.

Disclosed herein is an ion manipulation device for use in an inductively coupled plasma time-of-flight mass spectrometer, said ion manipulation device comprising a plurality of stacked ring electrodes gradually decreasing in radius and forming a funnel having an entrance at an end with a ring electrode of a largest radius and an exit at an end with a ring electrode of a smallest radius, wherein RF voltages of opposite polarities are applied to adjacent ring electrodes, and wherein DC voltages are applied separately to each ring electrode for controlling ion movement in an axial direction through the ring electrodes.

Disclosed herein is a method for manipulating targeted ions via an ion manipulation device for use in an inductively coupled plasma time-of-flight mass spectrometer, said method comprising providing a plurality of stacked ring electrodes gradually decreasing in radius and forming a funnel having an entrance at an end with a ring electrode of a largest radius and an exit at an end with a ring electrode of a smallest radius, applying RF voltages of opposite polarities to adjacent ring electrodes; and applying DC voltages separately to each ring electrode, thereby controlling ion movement in an axial direction through the ring electrodes. Amplitude of the RF voltages applied to the ring electrodes may be substantially constant from the entrance to the exit. An amplitude of the DC voltages applied to the ring electrodes may be substantially constant from the entrance to the exit. An amplitude of the DC voltages applied to the ring electrodes may be increased from the entrance to the exit. An amplitude of the DC voltages applied to the ring electrodes may be decreased from the entrance to the exit. Amplitude of the DC voltages applied to the ring electrode may be alternately increased or decreased from the entrance to the exit. An axial space between each of the ring electrodes may be substantially the same. An axial space between the ring electrodes may change along the length of the funnel. A thickness of each of the ring electrodes may be substantially the same. A thickness of the ring electrodes may change along the length of the funnel. The targeted ions may be manipulated along an axial direction through the plurality of stacked ring electrodes. The targeted ions may be metal isotope ions. The ion manipulation device may be configured to receive ions that have passed through an upstream perforated cone-shaped component. The ion manipulation device may be configured to receive ions from an upstream ion guide arrangement. The ion manipulation device may be configured to transport target ions to an ion guide arrangement configured to further guide the ions. The ion manipulation device may be configured to transport target ions for subsequent access by a time-of-flight (TOF) mass analyzer.

Disclosed herein is an ion manipulation device for use in an inductively coupled plasma time-of-flight mass spectrometer, said ion manipulation device comprising a first set of poles comprising a plurality of spaced apart segments along a length of each pole, said first set of poles arranged in a parallel manner with a space between the poles, wherein an RF voltage is applied to each pole of the first set of poles, and a second set of poles comprising a plurality of spaced apart segments along a length of each pole, said second set of poles arranged in a parallel manner and positioned in an alternating arrangement with respect to the first set of poles, wherein a minus RF voltage is applied to each pole of the second set of poles.

Disclosed herein is a method for manipulating targeted ions via an ion manipulation device for use in an inductively coupled plasma time-of-flight mass spectrometer, said method comprising providing a first set of poles comprising a plurality of spaced apart segments along a length of each pole, said first set of poles arranged in a parallel manner with a space between the poles, applying an RF voltage to each pole of the first set of poles, providing a second set of poles comprising a plurality of spaced apart segments along a length of each pole, said second set of poles arranged in a parallel manner and positioned in an alternating arrangement with respect to the first set of poles, and applying a minus RF voltage to each pole of the second set of poles. DC voltages may be applied on each segment to generate a DC potential gradient in an axial direction. An amplitude of the RF voltage applied to each segment in the first set of poles may remain the same along a length of the first set of poles. Amplitude of the minus RF voltage applied to each segment in the second set of poles may remain the same along a length of the second set of poles. An amplitude of the RF voltage applied to the segments in the first set of poles may be varied along a length of the first set of poles, thereby generating a RF pseudopotential gradient in an axial direction. An amplitude of the minus RF voltage applied to the segments in the second set of poles may be varied along a length of the second set of poles, thereby generating a RF pseudopotential gradient in an axial direction. A cross-section of a segment of the first set of poles may be a circle. A cross-sectional shape of a segment of the first set of poles may be an arc, a triangle, a trapezoid, or a rectangular bar. The targeted ions may be manipulated along an axial direction through the plurality of stacked ring electrodes. The targeted ions may be metal isotope ions. The ion manipulation device may be configured to receive ions that have passed through an upstream perforated cone-shaped component. The ion manipulation device may be configured to receive ions from an upstream ion guide arrangement. The ion manipulation device may be configured to transport target ions to an ion guide arrangement configured to further guide the ions. The ion manipulation device may be configured to transport target ions for subsequent access by a time-of-flight (TOF) mass analyzer.

Disclosed herein is an ion manipulation device for use in an inductively coupled plasma time-of-flight mass spectrometer, said ion manipulation device comprising a first set of rod electrodes arranged in a parallel manner with a space between the rod electrodes, wherein an RF voltage and a DC voltage is applied to the first set of rod electrodes, and a second set of rod electrodes arranged in a parallel manner and positioned in an alternating arrangement with respect to the first set of rod electrodes, wherein a DC voltage is applied to the second set of rod electrodes without application of an RF voltage.

Disclosed herein is a method for manipulating targeted ions via an ion manipulation device for use in an inductively coupled plasma time-of-flight mass spectrometer, said method comprising providing a first set of rod electrodes arranged in a parallel manner with a space between the rod electrodes, applying an RF voltage and a DC voltage to the first set of rod electrodes, providing a second set of rod electrodes arranged in a parallel manner and positioned in an alternating arrangement with respect to the first set of rod electrodes, and applying a DC voltage to the second set of rod electrodes without application of an RF voltage. A set of endcap electrodes may be positioned at ends of the first set of rod electrodes. A gap may be provided between the endcap electrodes and the first set of rod electrodes. A DC voltage may be applied to the set of endcap electrodes. RF voltages and the DC voltages may be selected to create an ion gate that determines a time length of an ion packet traveling through the ion manipulation device. A set of shorter rod electrodes positioned at ends of the first set of rod electrodes may be used. A gap may be provided between the shorter rod electrodes and the first set of rod electrodes. A DC voltage may be applied to the set of shorter rod electrodes. RF voltages and the DC voltages may be selected to create an ion gate that determines a time length of an ion packet traveling through the ion manipulation device. The targeted ions may be manipulated along an axial direction along a length of the first set of rod electrodes and the second set of rod electrodes. The targeted ions may be metal isotope ions. The ion manipulation device may be configured to receive ions that have passed through an upstream perforated cone-shaped component. The ion manipulation device may be configured to receive ions from an upstream ion guide arrangement. The ion manipulation device may be configured to transport target ions to an ion guide arrangement configured to further guide the ions. The ion manipulation device may be configured to transport target ions for subsequent access by a time-of-flight (TOF) mass analyzer.

Disclosed herein is an ion manipulation device for use in an inductively coupled plasma time-of-flight mass spectrometer, said ion manipulation device comprising a first set of poles comprising a plurality of spaced apart segments along a length of each pole, the first set of poles arranged in a parallel manner with a space between the poles, wherein an RF voltage is applied to each segment and a DC voltage is applied separately to each segment to form a DC potential gradient an axial direction to the first set of poles, and a second set of poles comprising a plurality of spaced apart segments along a length of each pole, the second set of poles arranged in a parallel manner and positioned in an alternating arrangement with respect to the first set of poles, wherein a DC voltage is applied separately to each segment to form a DC potential gradient an axial direction to the second set of poles without application of an RF voltage.

Disclosed herein is a method for manipulating targeted ions via an ion manipulation device for use in an inductively coupled plasma time-of-flight mass spectrometer, said method comprising providing a first set of poles comprising a plurality of spaced apart segments along a length of each pole, the first set of poles arranged in a parallel manner with a space between the poles, applying an RF voltage to each segment and a DC voltage separately to each segment to form a DC potential gradient an axial direction to the first set of poles, providing a second set of poles comprising a plurality of spaced apart segments along a length of each pole, the second set of poles arranged in a parallel manner and positioned in an alternating arrangement with respect to the first set of poles, and applying a DC voltage separately to each segment to form a DC potential gradient an axial direction to the second set of poles without application of an RF voltage. A set of endcap electrodes may be positioned at ends of the first set of poles. A gap may be provided between the endcap electrodes and the first set of poles. A DC voltage may be applied to the set of endcap electrodes. RF voltages and DC voltages may be selected to create an ion gate that determines a time length of an ion packet traveling through the ion manipulation device. A set of shorter rod electrodes positioned at ends of the first set of poles may be used. A gap may be provided between the shorter rod electrodes and the first set of poles. A DC voltage may be applied to the set of shorter rod electrodes. The RF voltages and the DC voltages may be selected to create an ion gate that determines a time length of an ion packet traveling through the ion manipulation device. The targeted ions may be manipulated along an axial direction along a length of the first set of poles and the second set of poles. The targeted ions may be metal isotope ions. The ion manipulation device may be configured to receive ions that have passed through an upstream perforated cone-shaped component. The ion manipulation device may be configured to receive ions from an upstream ion guide arrangement. The ion manipulation device may be configured to transport target ions to an ion guide arrangement configured to further guide the ions. The ion manipulation device may be configured to transport target ions for subsequent access by a time-of-flight (TOF) mass analyzer.

Additional aspects and advantages of the present disclosure will become readily apparent to those skilled in this art from the following detailed description, wherein only exemplary embodiments of the present disclosure are shown and described, simply by way of illustration of the best mode contemplated for carrying out the present disclosure. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The invention provides systems and methods for the analysis of single particles tagged with metal isotopes isolated from analytes, such as whole cells, microorganisms, viruses, etc. Various aspects of the invention described herein may be applied to any of the particular applications set forth below. The invention may be applied as a part of a mass spectrometry system comprising a sample introduction device, an ICP ionization device, an atmospheric pressure interface, an ion guide device, an ion manipulation device, a TOF mass analyzer, an ion detector, a signal processing device, or other devices. It shall be understood that different aspects of the invention can be appreciated individually, collectively or in combination with each other.

Figure 1:
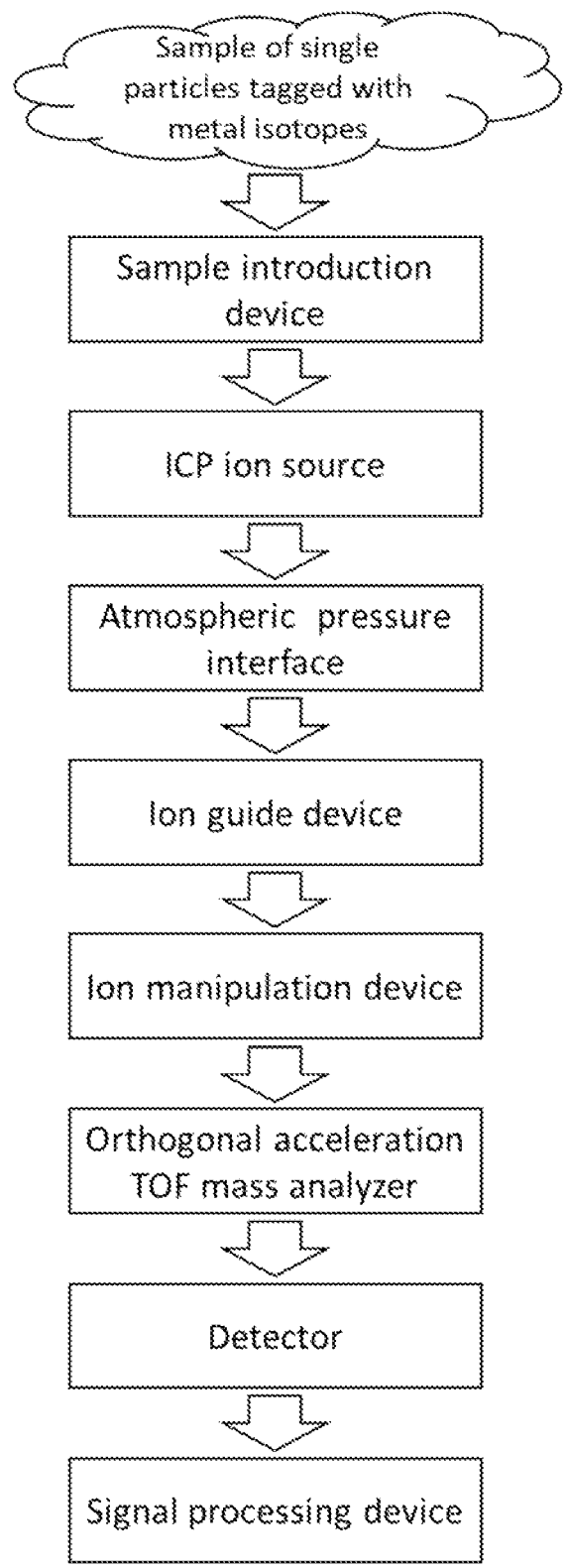
FIG. 1 shows a block diagram of ICP-TOF mass spectrometer disclosed in the invention for simultaneous multi-parameter analysis of a single particles tagged with metal isotopes, in accordance with embodiments of the invention.

FIG. 1 shows a block diagram of ICP-TOF mass spectrometry disclosed in the invention for simultaneous multi-parameter analysis of a single particle tagged with metal isotopes. The ICP-TOF MS comprises a sample introduction device, an ICP ionization device, an atmospheric pressure interface, an ion guide device, an ion manipulation device, a TOF mass analyzer, an ion detector and a signal processing device.

The sample introduction device can comprise a droplet generator, used to generate and deliver single particle droplets suitable for ICP TOF MS sampling. Single particles may include single cells, beads, polymer microspheres, biological molecules, or aerosols. Metal isotope tagged antibodies can be used to bind antigens found on or within a cell. Theoretically, over 100 antigens can be simultaneously detected in a single cell using unique metal isotope tags on corresponding antibodies. To avoid interference with elements found in cells, lanthanide elements are preferred as metal isotope tags. Examples of metal isotope tags can include lanthanum, cerium, prasedymium, neodymium, promethium, samarium, europium, gadolinium, terbium, dysprosium, holmium, erbium, thulium, ytterbium, lutetium, or any other isotope.

Single particles may be encapsulated in a carrier. For instance, a single cell may be encapsulated in a carrier. The carrier may form a droplet that may partially or completely surround the particle. The particle may be suspended within the carrier droplet.

The carrier may be a carrier fluid, such as water, mixture of water and oil, and mixture of water and organic solvent. The droplet generator may yield individual sample droplets which may include particles within the carrier fluid droplets.

The sample introduction device can be used to transport single particles tagged with metal isotopes into an ICP ionization device wherein they can be evaporated, atomized, and ionized to generate ions of metal isotopes.

The ions can be moved into an atmospheric pressure/vacuum interface from where they are placed into a vacuum. The ions can then be transported by an ion guide device into an ion manipulation device downstream. Within the ion manipulation device, ions can be further processed to refine the ions prior to entering the TOF mass analyzer, such as undergoing duty cycle. Within the TOF mass analyzer, ions are separated and arrive at an ion detector sequentially. The ion signal generated from the ion detector is processed by the signal processing device which generates a mass spectrum.

Figure 2A:
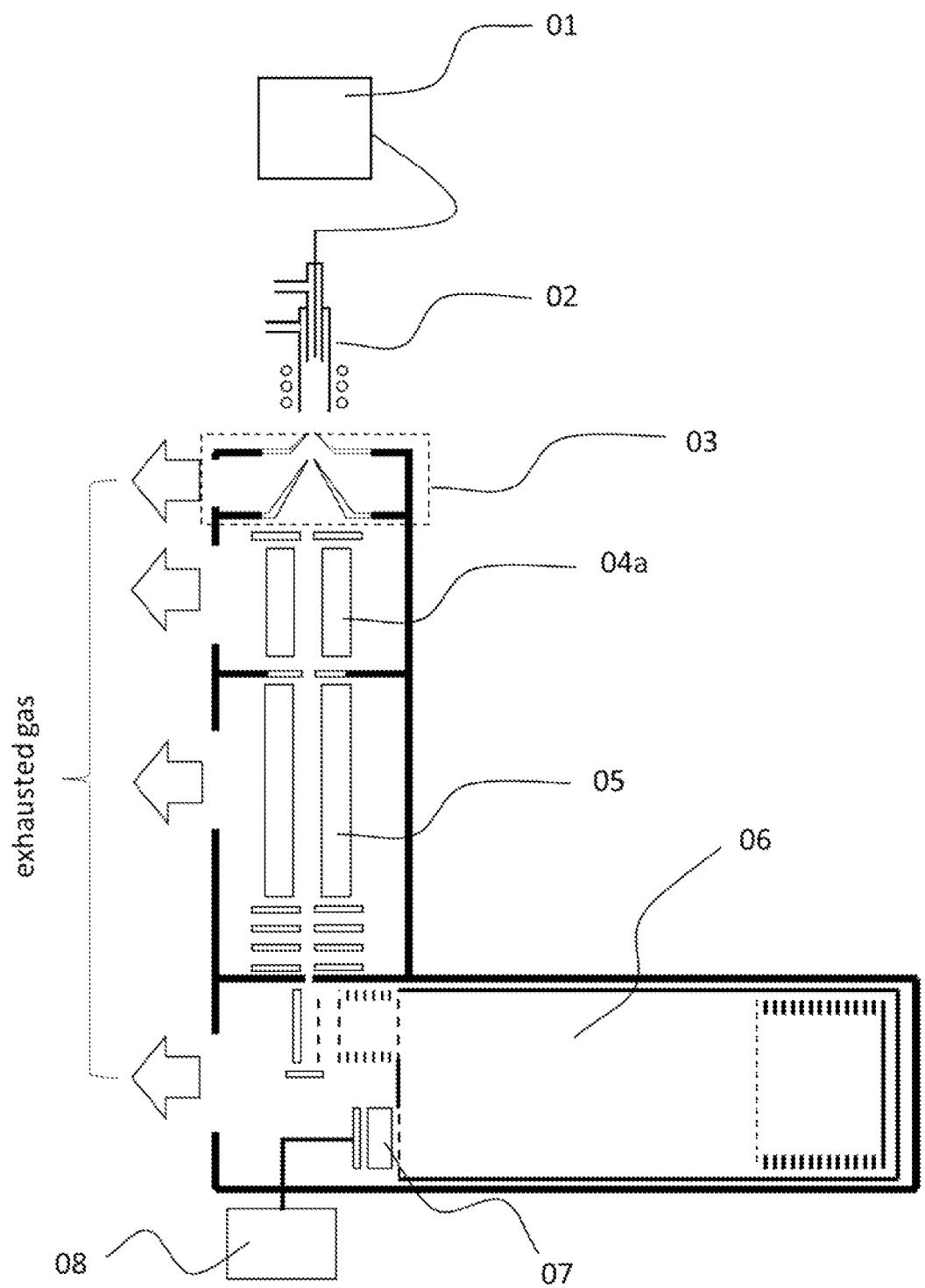
FIG. 2A and FIG. 2B each shows a schematic of ICP-TOF mass spectrometer based on traditional instrument layout for simultaneous multiparameter analysis of single particles tagged with metal isotopes, in accordance with embodiments of the invention.

FIG. 2A shows an exemplary structure of an ICP-TOF MS. Antibodies tagged with different metal isotopes are mixed with samples of particles. The antibodies specifically bind to target antigens, hereafter particles, thereby tagging the particles.

The tagged particles are transported by the sample introduction device 01 to the ICP ionization device 02 sequentially. The sample introduction device 01 is used to perform necessary processes on the sample of particles tagged with metal isotopes in order to generate a sequence of single particles in the gas phase before transport to the ICP ionization device 02.

Within the ICP ionization device, the particles are individually evaporated, atomized and ionized to generate monoatomic or polyatomic ions. Ions of the metal isotopes used to tag the particles are formed in the ICP ionization device 02. Alternatively, the ICP ionization device can be replaced by a microwave plasma torch (MPT), glow discharge ionization (GDI), or laser ionization (LI) among others.

The metal isotope ions are then placed into a vacuum through the atmospheric pressure interface 03. The atmospheric pressure interface 03 can comprise 2-3 cone-shaped components. The atmospheric pressure interface 03 contains two perforated cone-shaped components separating two adjacent vacuum chambers. The hole size limits the volume of gas that can pass through each component. There can be a corresponding vacuum pump for each vacuum chamber allowing the gas pressure to gradually decrease from upstream to downstream. The pressure drop can be greatest near the boundary of the two chambers, noted by the dotted rectangle as the region near the perforated cone-shaped components. This pressure drop is referred to as a supersonic expansion. The shape, hole size, inter distance and voltages applied to the vacuum chamber can be optimized depending on the application.

After that, the metal isotope ions are transported to an ion guide device 04a. The ion guide device 04a can receive the metal isotope ions from the upstream perforated cone-shaped components. The ion guide device 04 can be chosen from an electrostatic lens, a quadrupole, a multipole, an ion tunnel, an ion funnel, etc.

A linear ion guide device 04a is shown. However, curved ion guide devices provide several advantages including (1) removing neutral noise from a variety of gas molecules in the environment to increase the signal to noise ratio and decrease the gas burden of the vacuum pump, and (2) increasing the flexibility of the instrument design by decreasing the instrument footprint. The ion guide may be shaped so as to provide a 90 degree turn or a 180 degree turn in the focused ion path. Any degree turn may be provided with further examples provided herein. Alternatively, the straight sections of the ion guide with a 90 degree turn or a 180 degree turn may be extended by providing linear ion guide section adjacent to the ion inlet and the ion outlet of the ion guide with a 90 degree turn or a 180 degree turn. Alternatively, two 90 degree ion guides may be positioned adjacent to one another to realize a 180 degree turn in the ion path. Alternatively, two similarly shaped curved ion guides may be positioned adjacent to one another such that the radius of curvature of one ion guide is directed oppositely to that of the other ion guide, thereby providing an S-shaped ion path.

Once in the ion guide device 04a, the metal isotope ions are directed into a downstream ion manipulation device 05. The ion manipulation device 05 is used to process the metal isotope ions from the ion guide device 04a according to a variety of practical requirements including at least one of the following: (1) selectively filtering ions with a specific mass, (2) ion bunching; or (3) ion storage. The purpose of processing ions is to improve the performance, including duty cycle, resolution, space charge and so on, of the downstream devices.

After modulation in the downstream ion manipulation device 05, the metal isotope ions are directed to an optional ion shaping device. The ion shaping device can be configured to regulate an angle of divergence of metal isotope ions, such that a cross-sectional shape and size of the metal isotope ions can be regulated. In an example, the angle of divergence of metal isotope ions can be reduced in the ion shaping device to reduce a cross-sectional shape and size of the metal isotope ions. The regulated metal isotope ions can then be directed to a TOF mass analyzer 06. The processed ions fly into the orthogonal acceleration region 06a in the TOF mass analyzer 06, wherein they can be accelerated by a pulse acceleration voltage. The accelerated ions can separate in space and arrive at the ion detector 07.

Ions with different masses are separated in the TOF mass analyzer 06 and arrive at the ion detector 07 sequentially to generate an ion flow signal.

The present disclosure allows for the effective identification of metal isotopes and the corresponding antigens of single cells both qualitatively and quantitatively in the mass spectrum. The ion flow signal is processed by the signal processing device 08 to generate a final mass spectrum. The signal processing device 08 can be used to process the ion flow signal to generate the final mass spectrum for qualitative and quantitative identification of the metal isotopes.

Figure 2B:
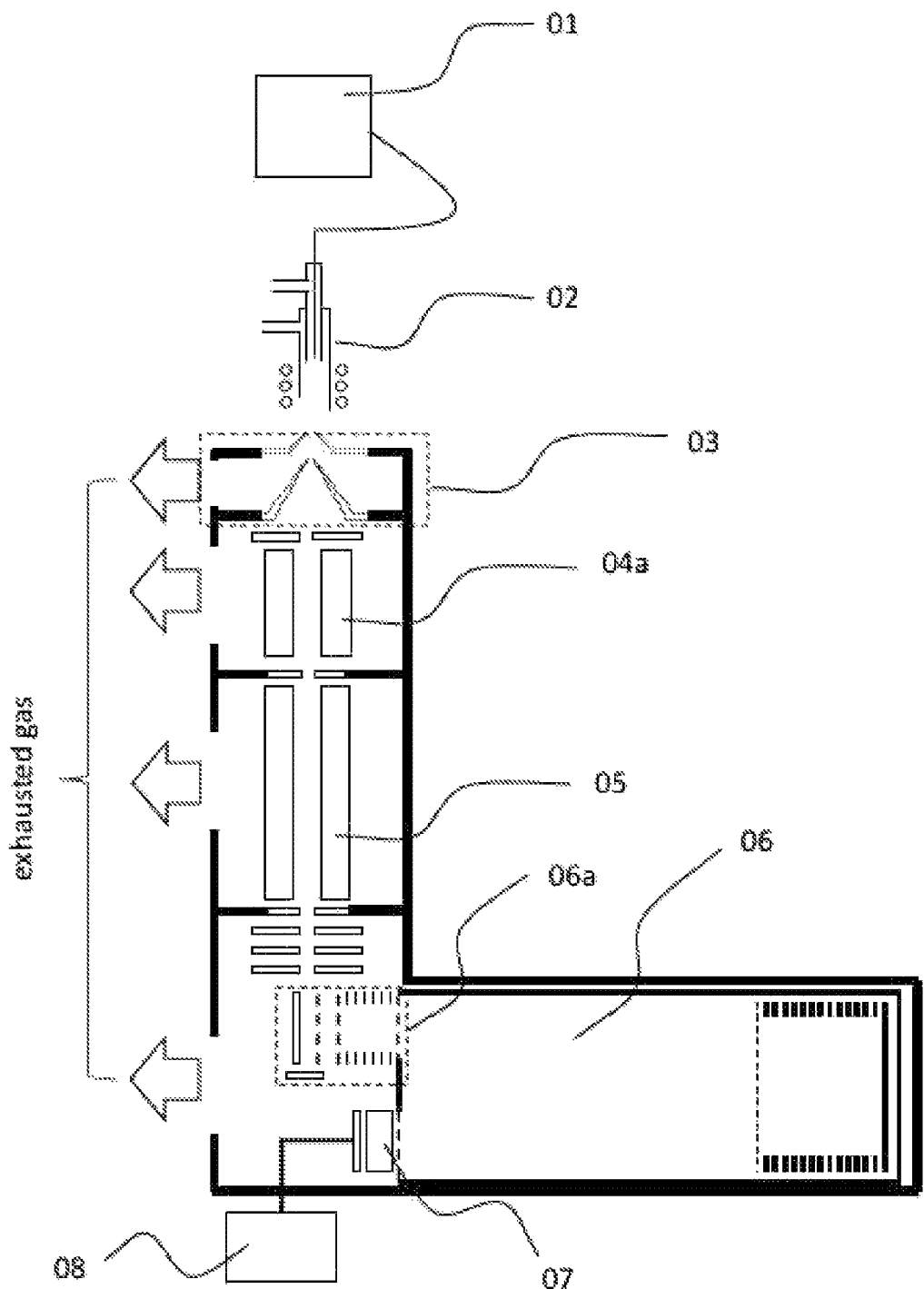

FIG. 2B shows another exemplary structure of an ICP-TOF MS. The structure of an ICP-TOF MS shown in FIG. 2B can be substantially similar to that shown in FIG. 2A except that, in the configuration of the ICP-TOF MS of FIG. 2B, the ion shaping device is positioned in the same vacuum chamber with the ion manipulation device 05, however in the configuration shown in FIG. 2A, the ion shaping device is positioned in the same vacuum chamber with the TOF mass analyzer 06. The ion shaping device can be positioned at different portions or adjacent to various components of the ICP-TOF MS, and configurations are not limited to the illustrations provided herein.

Figure 3A:
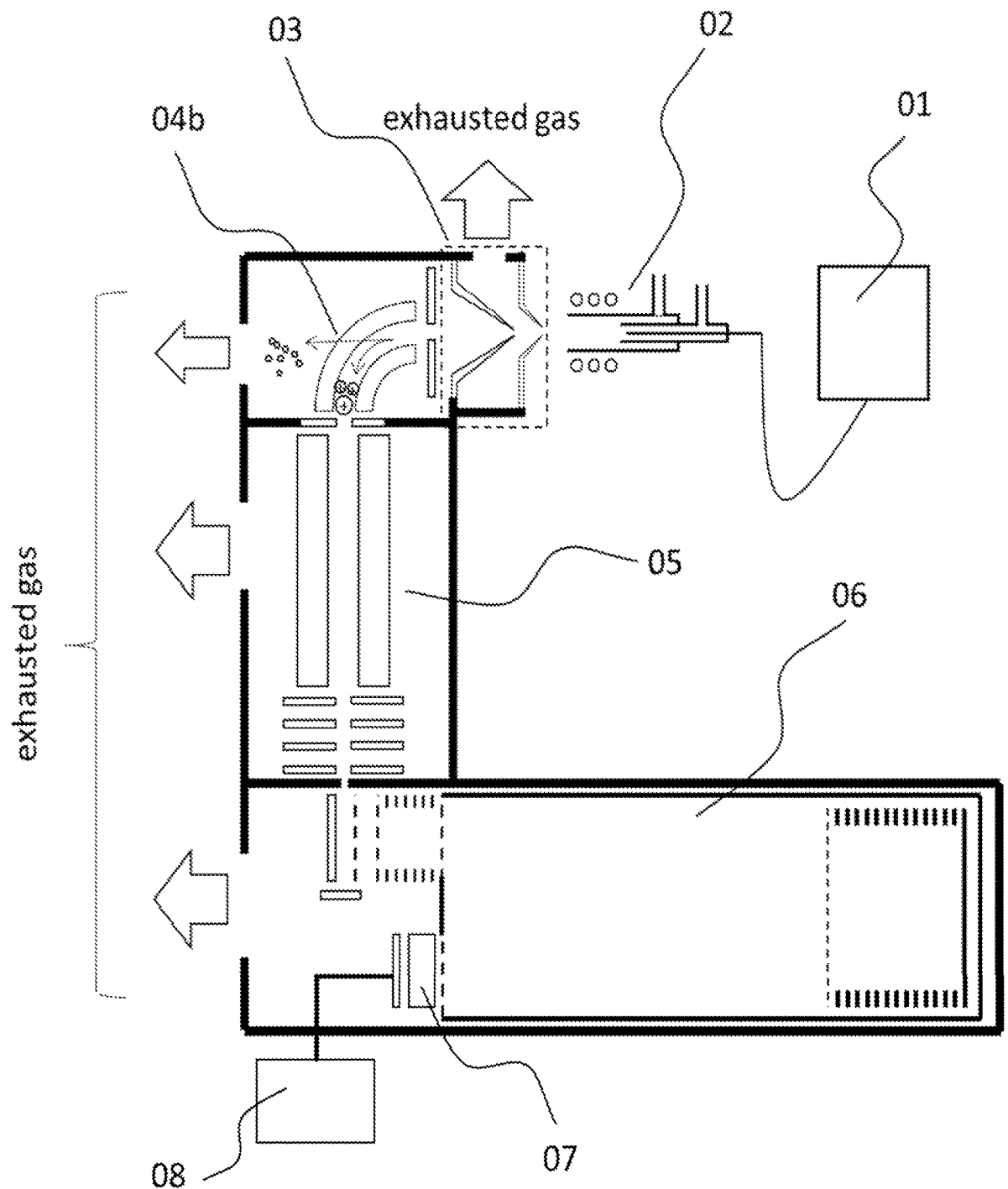
FIG. 3A and FIG. 3B each shows a schematic of ICP-TOF mass spectrometer using a curved ion guide device for simultaneous multiparameter analysis of single particles tagged with metal isotopes wherein neutral gas molecules are not confined by the electric field ion guide device, so most of them will be pumped out directly by vacuum pump, in accordance with embodiments of the invention.

FIG. 3A shows an instrument layout using a curved ion device 04b placed between the atmospheric pressure interface 03 and the ion manipulation device 05. Alternatively, one or more curved ion guide devices can be used with varying degrees of curvature. Degrees of curvature can include less than or equal to 90 degrees, 95 degrees, 100 degrees, 105 degrees, 110 degrees, 115 degrees, 120 degrees, 125 degrees, 130 degrees, 135 degrees, 140 degrees, 145 degrees, 150 degrees, 155 degrees, 160 degrees, 165 degrees, 170 degrees, 175 degrees, or 180 degrees.

Figure 3B:
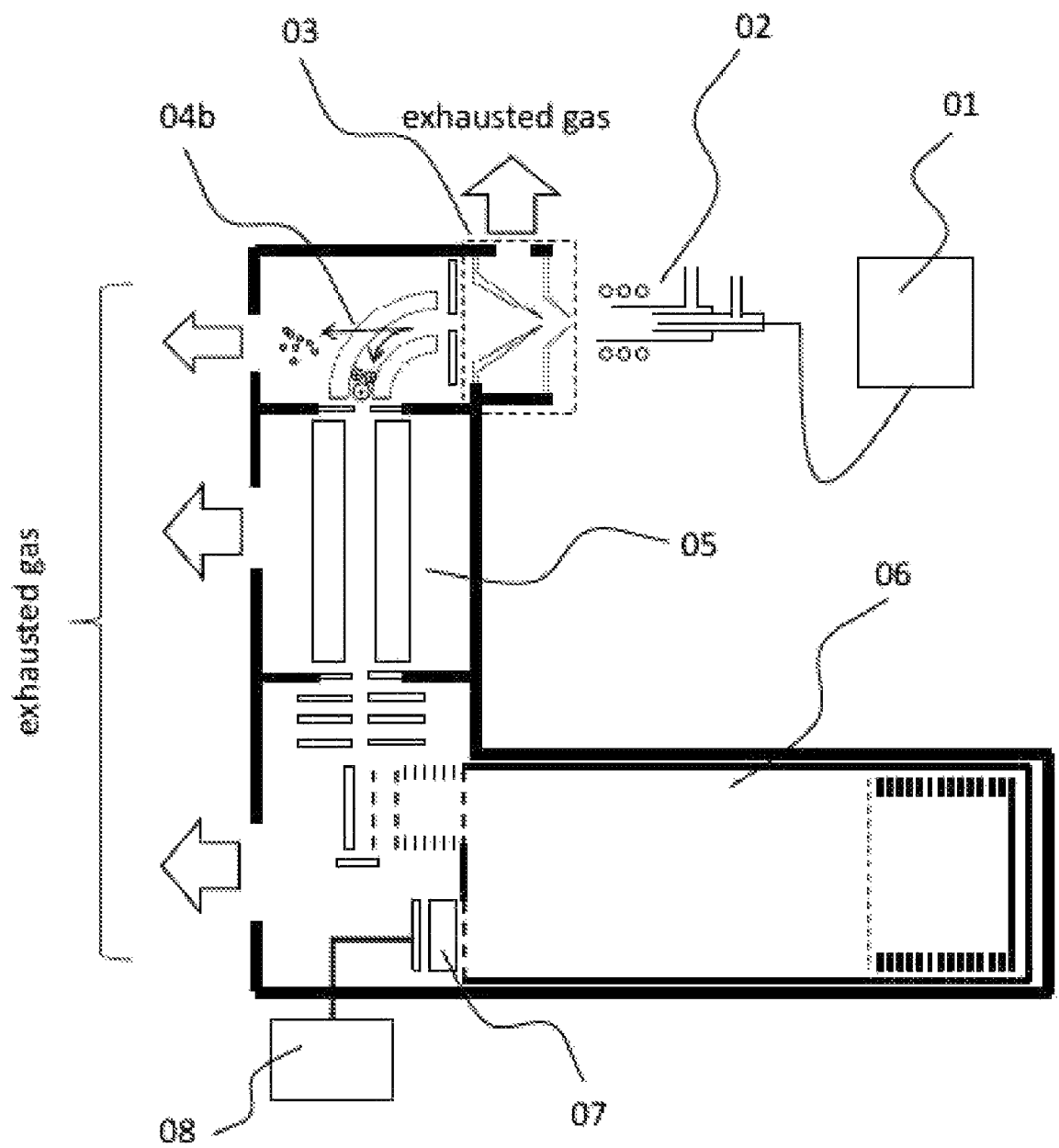

FIG. 3B shows another example of instrument layout using a curved ion device 04b. The structure shown in FIG. 3B can be substantially similar to that shown in FIG. 3A except that, in the structure of FIG. 3B, the ion shaping device is positioned in the same vacuum chamber with the ion manipulation device 05, however in the structure shown in FIG. 3A, the ion shaping device is positioned in the same vacuum chamber with the TOF mass analyzer 06.

Figure 4A:
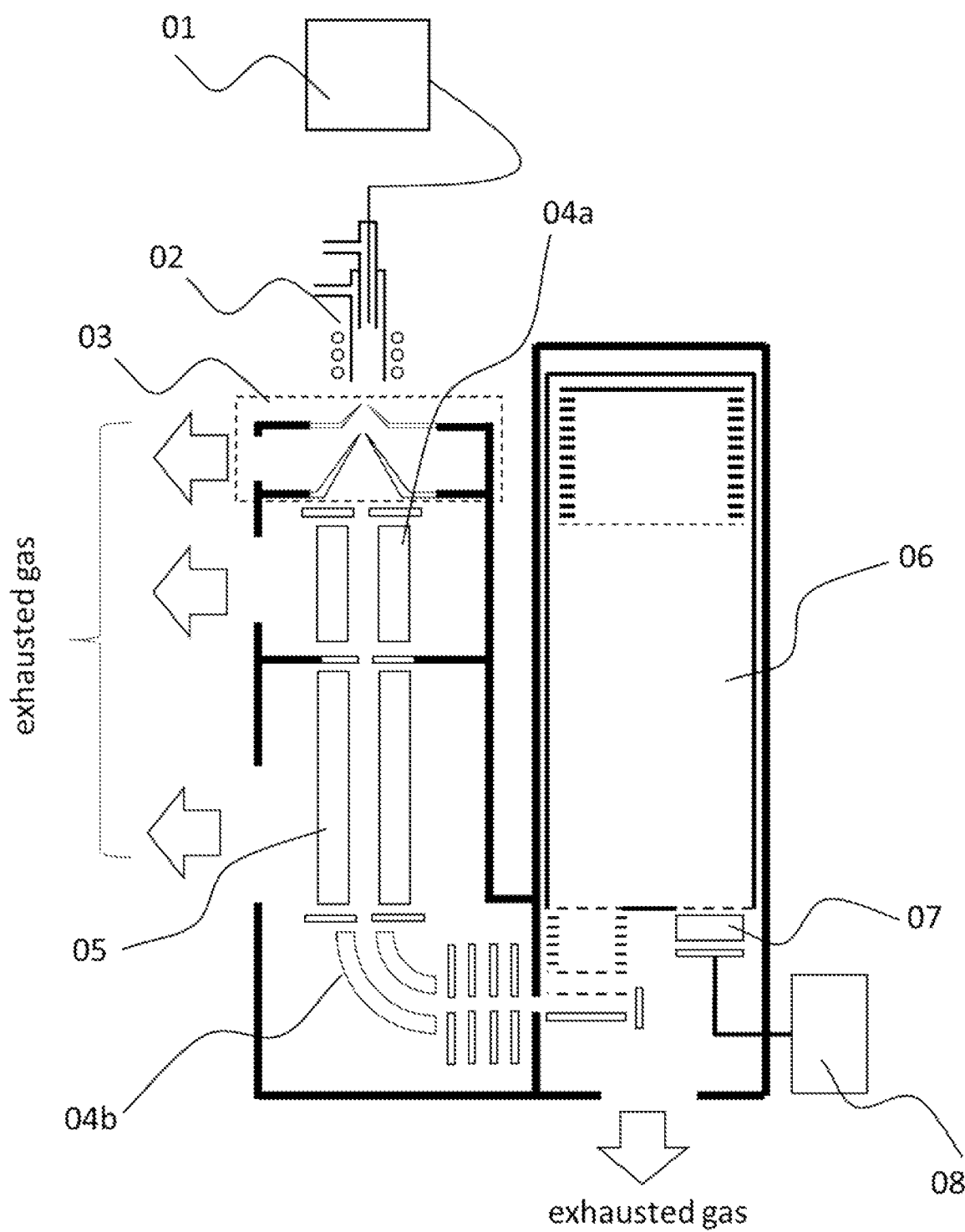
FIG. 4A and FIG. 4B each shows a schematic of ICP-TOF mass spectrometer using a curved ion guide device for simultaneous multiparameter analysis of a single particle tagged with metal isotopes, in accordance with embodiments of the invention.

FIG. 4A is another example of an instrument layout using a curved instrument guide device 04b arranged between the ion manipulation device 05 and the TOF mass analyzer 06 as well as a linear ion guide device 04a arranged between an atmospheric pressure interface 03 and an ion manipulation device 05. Alternatively, one or more curved ion guide devices can be used with varying degrees of curvature. Degrees of curvature include less than or equal to 90 degrees, 95 degrees, 100 degrees, 105 degrees, 110 degrees, 115 degrees, 120 degrees, 125 degrees, 130 degrees, 135 degrees, 140 degrees, 145 degrees, 150 degrees, 155 degrees, 160 degrees, 165 degrees, 170 degrees, 175 degrees, or 180 degrees.

Disclosed herein are examples of ion guide 04 elements which may allow for greater control of the flight path of single particles tagged with metal isotope ions. Such control may be desirable when analyzing a complex sample comprising a large variety of species of single particles tagged with metal isotope ions. Such elements may include linear electrodes, curved electrodes, quadrupoles, ion tunnel devices, and combinations thereof. Voltages applied may include direct current (DC), radio frequency (RF), and stored-waveform inverse Fourier transform (SWIFT). Curved electrodes may comprise concave or convex surfaces in combination with linear surfaces. Ion tunnel devices may be comprised of sets of rings of the same size or differing sizes. Ion tunnel devices may be comprised of axially segmented quadrupoles or multipoles of the same size or differing sizes. Quadrupoles and multipoles may be arranged in a curved configuration, a v-shaped configuration, an S-shaped configuration, and any variation of the configurations described herein.

Figure 4B:
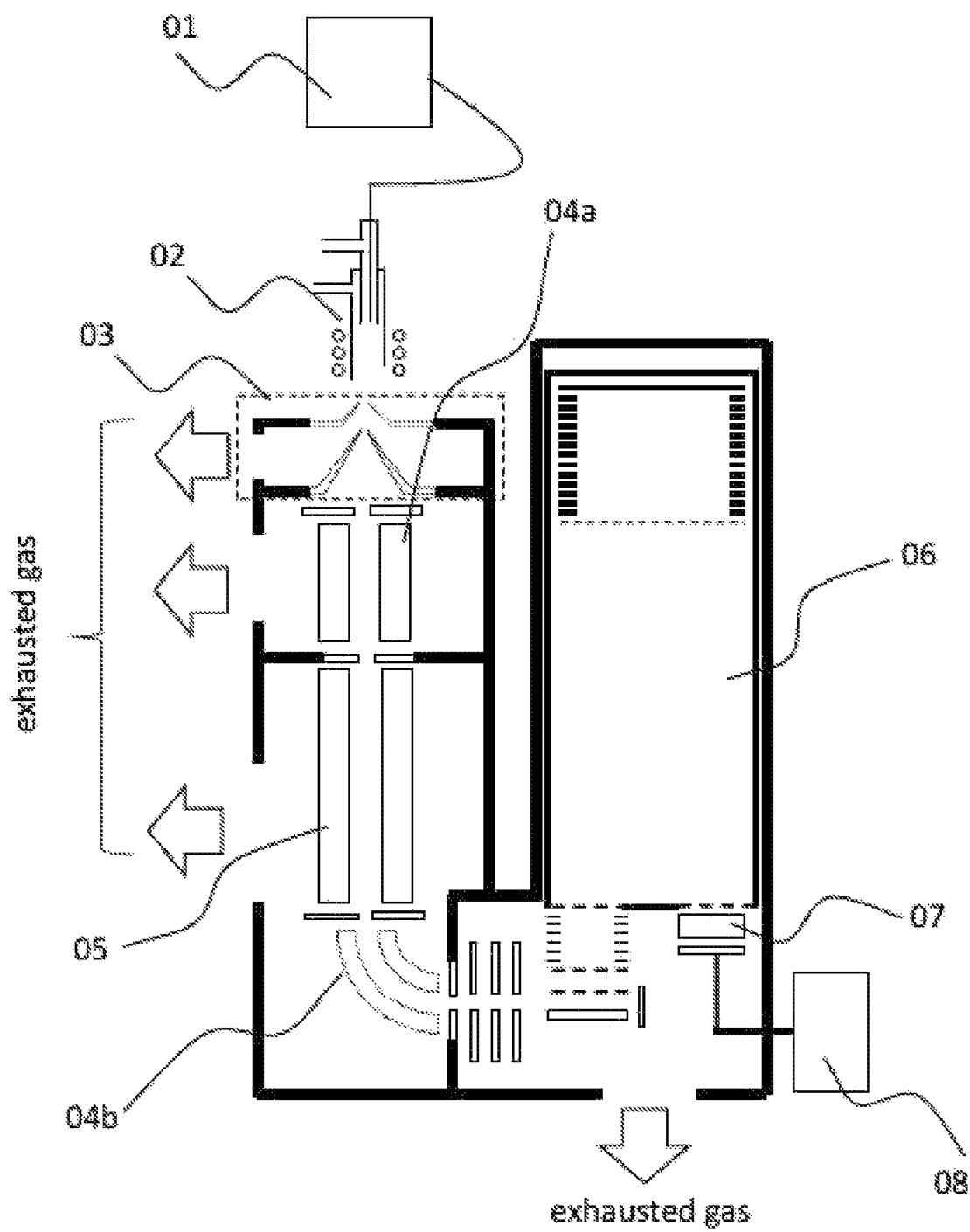

FIG. 4B shows another example of an instrument layout using a curved instrument guide device 04b arranged between the ion manipulation device 05 and the TOF mass analyzer 06. The structure shown in FIG. 4B can be substantially similar to that shown in FIG. 4A except that, in the structure of FIG. 4B, the ion shaping device is positioned in the same vacuum chamber with the ion manipulation device 05, however in the structure shown in FIG. 4A, the ion shaping device is positioned in the same vacuum chamber with the TOF mass analyzer 06.

Figure 5:
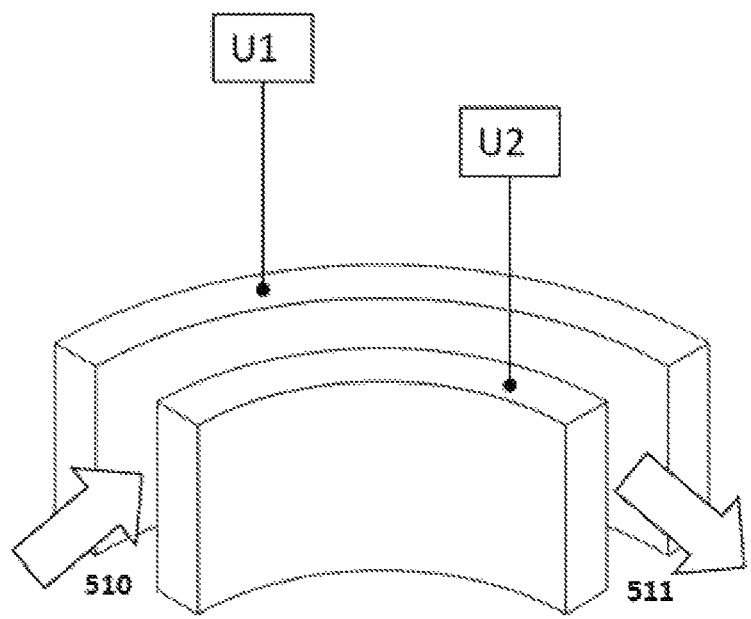
FIG. 5 shows a comparison of electrostatic sectors used as a curved ion guide device in ICP-TOF mass spectrometer. In (a), the two curved electrodes have a flat surface and in (b) the electrodes have both convex and concave surfaces, in accordance with embodiments of the invention.
Figure 5:
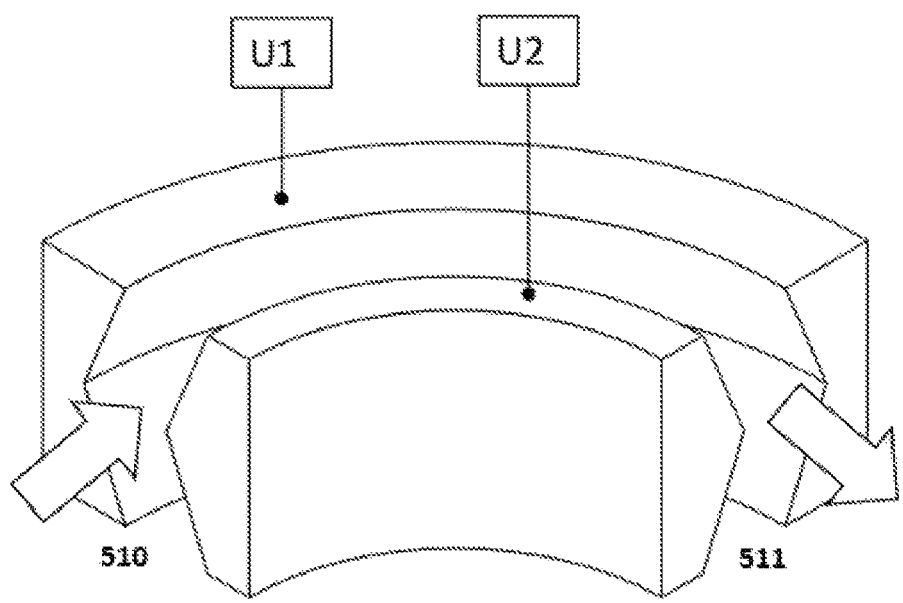

FIG. 5 shows an example of an ion guide device, in accordance with embodiments of the invention. The ion guide may improve the efficiency of ion focusing. The ion guide device may comprise a curved electrostatic sector. The ion guide may curve. The ion guide may curve so that an outer surface (e.g., convex surface) of the curve is to the right, or the ion guide may curve so that an inner surface (e.g., concave surface) of the curve is to the right. In some instances, the curve may occur in a lateral direction. Optionally, the curve may occur in a vertical direction (e.g., upwards or downwards). The curve may occur in any direction with respect to a direction of gravity. The electrostatic sector can be curved or flat.

The ion guide device may comprise two or more electrodes U1, U2. The electrodes may be generally parallel to each other. Each electrode may comprise one or more working surfaces. The working surfaces of the electrodes may face one another. A gap may be provided between the working surfaces. The region between the working surfaces may be an ion channel. As appreciated by persons skilled in the art, upon proper application of voltages to the electrodes, the electrodes generate an electric field that focuses ions generally along a curved path represented by the arrows. Owing to the curved geometry of the ion guide, the respective axes of the first end of the ion guide 510 and the second end of the ion guide 511 are not collinear. Only charged particles may be influenced by the electric field. A particle stream may contain ions and neutral particles (e.g., gas molecules, liquid droplets, etc.). Upon entering the ion guide through the first end of the ion guide 510, ions are constrained to motions in the vicinity of the central axis between the electrodes while the neutral ions may generally continue on a straight path. Consequently, only ions may exit the ion guide through the second end of the ion guide 511.

The ion guide device can comprise working surfaces which can be flat, curved, smooth, grooved, rough, concave, convex, or any combination thereof. FIG. 5a shows an example of an ion guide device comprising a pair of electrodes with flat working surfaces. FIG. 5b, shows an example of an ion guide device comprising a first electrode U1 with a concave working surface and a second electrode U2 with a convex working surface.

The direction of ion transmission in the ion channel can be axial. The direction of ion transmission may be perpendicular to a radial axis of the curved ion channel. The direction of ion transmission may be along a length of the ion channel.

Ion guides herein described may have overall lengths of 1 to 40 centimeters (cm). For example, the overall length can be about 1-2, 2-5, 5-7.5, 7.5-10, 10-15, 15-20, 20-25, 25-30, 30-35, or 35-40 cm. In some instances, the overall length can be on the scale of 0.1 cm, 1 cm, 10 cm, or 100 cm. The ion channel may have an inscribed diameter of about 0.5 to 30 millimeters (mm). For example, the ion channel inscribed diameter may be about 1-2, 2-4, 4-6, 6-8, 8-10, 10-12, 12-14, 14-16, 16-18, 18-20, 20-22, 22-24, 24-26, 26-28, or 28-30 mm. The diameter of the electrodes of the ion guide may be about 0.5 to 20 mm. For example, an electrode diameter may be about 0.5-1, 1-2, 2-4, 4-6, 6-8, 8-10, 10-12, 12-14, 14-16, 16-18, or 18-20 mm. Dimensions outside these ranges may also be useful in some applications.

The distance between electrodes may be the same through the length of the ion guide device. The distance between electrodes may vary along the length of the ion guide device. The distance between electrodes may increase from a first end of the ion guide 510 to a second end of the ion guide 511. The distance between electrodes may decrease from a first end of the ion guide 510 to a second end of the ion guide 511. The distance between electrodes may alternatively increase and decrease from a first end of the ion guide device 510 to a second end of the ion guide 511. The distance between electrodes may decrease from a top side to a bottom side of the ion guide device. The distance between electrodes may increase from a top side to a bottom side of the ion guide device. The distance between electrodes may alternatively increase and decrease from a top side to a bottom side of the ion guide device.

One or more voltages may be applied to the plurality of electrodes in order to urge ions along at least a portion of the length of the ion guide. One or more non-zero DC voltage gradients may be applied or maintained along at least a portion of the length of the ion guide. One or more transient DC voltages or transient DC voltage wave forms may be applied to at least some of the electrodes in order to urge at least some ions along at least a portion of the length of the ion guide. One or more DC potential wells may be formed at different positions within the ion guide to control an ion path through the ion guide. One or more DC potential wells may be formed at different times within the ion guide to control an ion path through the ion guide. The height, depth, and width of the DC potential well may be increased or decreased along or around the length of the ion guide.

Figure 6:
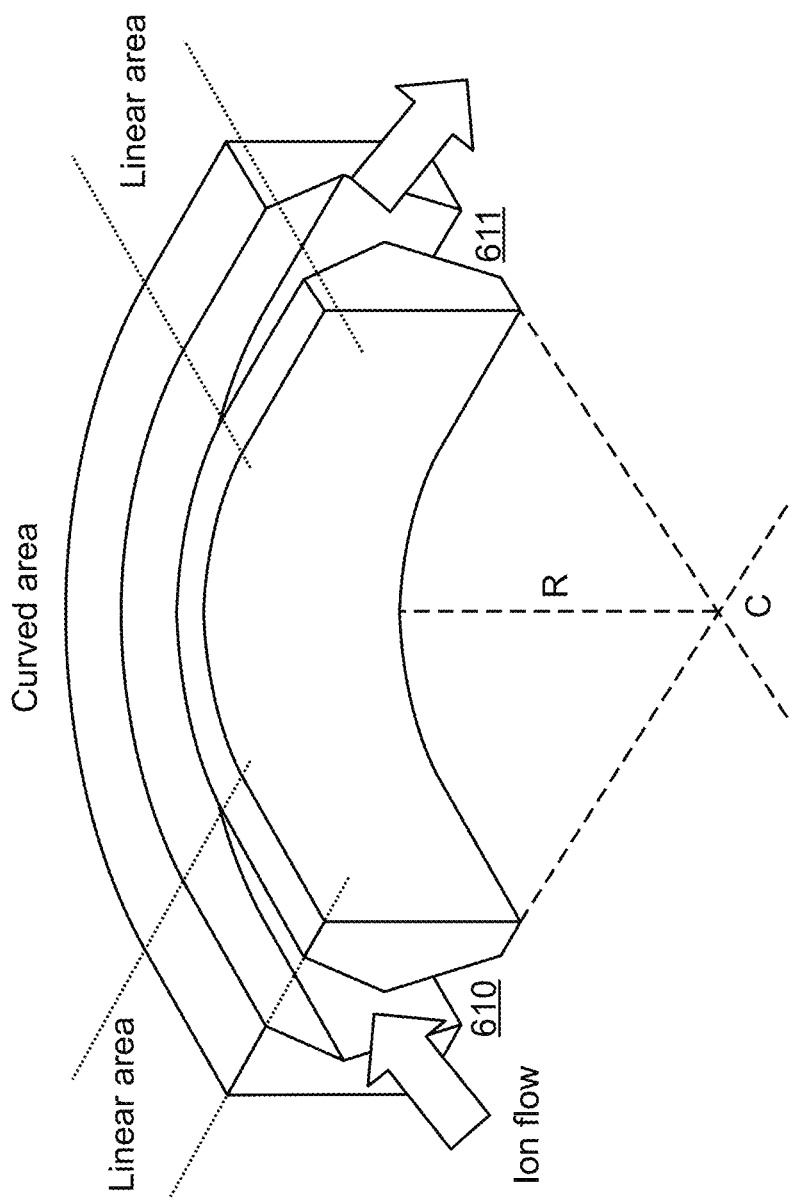
FIG. 6 shows a diagram of an electrostatic sector with two linear areas located and two ends and one curved area located in the middle, in accordance with embodiments of the invention.

FIG. 6 shows a curved electrostatic sector in which two linear regions are at two ends, 610 and 611, and one curved region is in the center. The purpose of adding linear regions at the end is to adjust the kinetic energy of ions before they enter the curved region, thereby filtering out interference ions which are unable to make it through the curved region.

The central axis may be conceptualized as running coextensively along the arc of a circular section defined by a center of curvature C and a radius of curvature R, with the radius of curvature R being the radial distance between the central axis and the center of curvature C. The central axis may extend along any length of arc of the circle of which the circular section is a part. The radius of curvature may be about 10 millimeters (mm) to 20 mm, 20 to 30 mm, 30 mm to 40 mm, 40 mm to 50 mm, 50 mm to 60 mm, 60 mm to 70 mm, 70 mm to 80 mm, 80 mm to 90 mm, 90 mm to 100 mm, 100 mm to 110 mm, 110 mm to 120 mm, 120 mm to 130 mm, 130 mm to 140 mm, 140 mm to 150 mm, 150 mm to 160 mm, 160 mm to 170 mm, 170 mm to 180 mm, 180 mm to 190 mm, or 190 mm to 200 mm. The radius of curvature may be greater than about 10 millimeters (mm), 20 mm, 30 mm, 40 mm, 50 mm, 60 mm, 70 mm, 80 mm, 90 mm, 100 mm, 110 mm, 120 mm, 130 mm, 140 mm, 150 mm, 160 mm, 170 mm, 180 mm, 190 mm, or 200 mm. The radius of curvature may be less than about 200 mm, 190 mm, 180 mm, 170 mm, 160 mm, 150 mm, 140 mm, 130 mm, 120 mm, 110 mm, 100 mm, 90 mm, 80 mm, 70 mm, 60 mm, 50 mm, 40 mm, 30 mm, 20 mm, or 10 mm.

One or more linear regions can be in direct contact with the curved section of the curved section of the first electrode. One or more linear regions can be in direct contact with the curved section of the second electrode. The curved section of the first electrode can be positioned between at least two linear sections. The curved section of the second electrode can be positioned between at least two linear sections. Alternatively, or in combination, the first electrode and the second electrode can comprise a same cross-sectional shape along a length of the first electrode and the second electrode. The ratio of curved length of an electrode to linear length of an electrode may be about 1:1, 1:2, 1:3, 1:4, 1:5, 1:6, 1:7, 1:8, 1:9, 1:10. The ratio of linear length of an electrode to curved length of an electrode may be about 1:1, 1:2, 1:3, 1:4, 1:5, 1:6, 1:7, 1:8, 1:9, 1:10. The curved length may be about 20 millimeters (mm) to 30 mm, 30 mm to 40 mm, 40 mm to 50 mm, 50 mm to 60 mm, 60 mm to 70 mm, 70 mm to 80 mm, 80 mm to 90 mm, 90 mm to 100 mm, 100 mm to 110 mm, 110 mm to 120 mm, 120 mm to 130 mm, 130 mm to 140 mm, 140 mm to 150 mm, 150 mm to 160 mm, 160 mm to 170 mm, 170 mm to 180 mm, 180 mm to 190 mm, or 190 mm to 200 mm. The curved length may be greater than about 10 millimeters (mm), 20 mm, 30 mm, 40 mm, 50 mm, 60 mm, 70 mm, 80 mm, 90 mm, 100 mm, 110 mm, 120 mm, 130 mm, 140 mm, 150 mm, 160 mm, 170 mm, 180 mm, 190 mm, or 200 mm. The curved length may be less than about 200 mm, 190 mm, 180 mm, 170 mm, 160 mm, 150 mm, 140 mm, 130 mm, 120 mm, 110 mm, 100 mm, 90 mm, 80 mm, 70 mm, 60 mm, 50 mm, 40 mm, 30 mm, 20 mm, or 10 mm. The linear length may be about 0 mm to 10 mm, 10 mm to 20 mm, 20 mm to 30 mm, 30 mm to 40 mm, 40 mm to 50 mm, 50 mm to 60 mm, 60 mm to 70 mm, 70 mm to 80 mm, 80 mm to 90 mm, or 90 mm to 100 mm. The linear length may be greater than about 10 millimeters (mm), 20 mm, 30 mm, 40 mm, 50 mm, 60 mm, 70 mm, 80 mm, 90 mm, or 100 mm. The linear length may be less than about 100 mm, 90 mm, 80 mm, 70 mm, 60 mm, 50 mm, 40 mm, 30 mm, 20 mm, or 10 mm.

One or more regions of the electrode can be linear or curved. Each region can be a section of a single integral piece. Each region can be an individual electrode coupled together to form a single electrode. Each individual electrode may be comprised of the same material. Each individual electrode may be comprised of a different material respective to each other.

The first electrode can comprise a concave surface. The concave surface can comprise a first planar surface and a second planar surface which meets the first planar surface without being parallel to the first planar surface. The concave surface can extend along the curved section of the first electrode and one or more linear sections adjacent to the curved section. The second electrode can comprise a convex surface, wherein the surface comprises a third and fourth planar surfaces. The fourth planar surface can meet the third planar surface without being parallel. The concave surface can extend along the curved section of the second electrode wherein one or more linear sections are adjacent to the curved section. Alternatively, or in combination, the concave surface of the first curved electrode can directly face the convex surface of the second curved electrode. In one embodiment, a length of the concave surface of the first curved electrode can curve inward. Alternatively, or in combination, a length of the convex surface of the second curved electrode can curve outward. Alternatively, or in combination, the surface of the first electrode can comprise a surface that alternates between a convex and a concave shape. The surface of the second electrode may comprise a shape complementary to the first electrode or may comprise a surface that alternates between a complementary shape to the first electrode and a mirroring shape to the first electrode. Electrodes can comprise metals including but not limited to tungsten, molybdenum, stainless steel, aluminum, copper, or gold coated quartz.

The ion guide can focus ions radially upon application of a voltage to the first and second electrode. The ion guide can be configured to guide ions around at least an angle of 90 degrees, 95 degrees, 100 degrees, 105 degrees, 110 degrees, 115 degrees, 120 degrees, 125 degrees, 130 degrees, 135 degrees, 140 degrees, 145 degrees, 150 degrees, 155 degrees, 160 degrees, 165 degrees, 170 degrees, 175 degrees, or 180 degrees.

Figure 7:
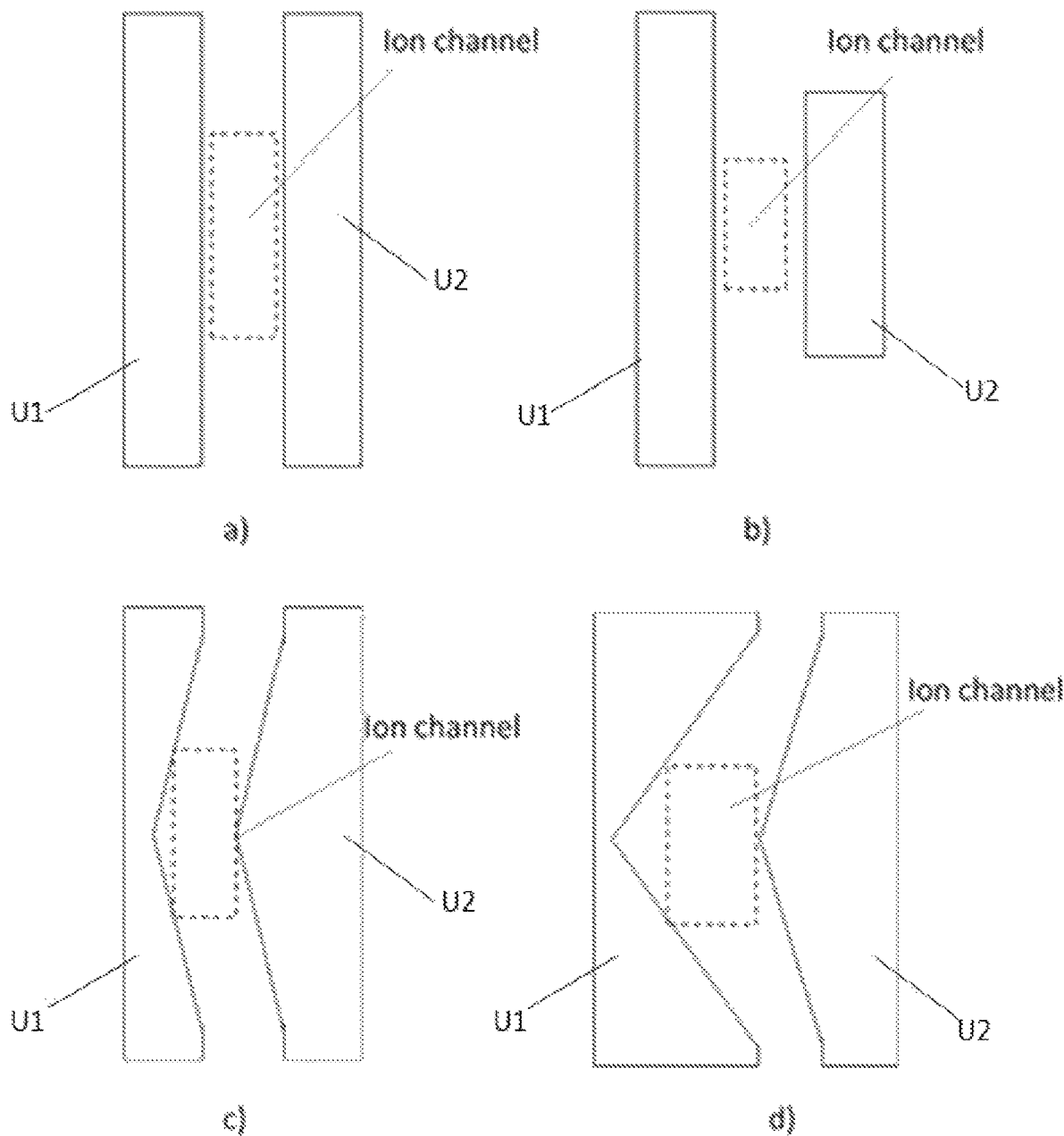
FIG. 7 shows a cross section of electrodes used in the electrostatic sectors in the radial direction. Panel (a) and (b) show the flat surface of the prior art wherein panel (c) and (d) show the non-parallel structures of the present disclosure, in accordance with embodiments of the invention.

FIG. 7, panel a and b show radial cross sections of a traditional electrostatic sector wherein the working surface is flat. The intersecting line between the working surface and the radial cross section is a broken line to indicate that the flat surface deflects ions without focusing the ions radially. Although the radial cross section of the configuration shown in panel b has an effect on radial ion focusing, the ion capacity is limited. Panels c and d show a radial cross sections of the present disclosure wherein the working surface is comprised of non-parallel structures which enhances the performance of the ion guide to focus ions radially. Examples of non-parallel structures may include structures wherein a first side U1 comprises a larger angle than the opposing side U2, wherein a second side U2 comprises a larger angle than the opposing side U1. Alternatively, or in combination, U1 may comprise a higher ratio of straight to curved surface area than U2. U2 may comprise a higher ratio of straight to curved surface area than U1.

The ion guide can comprise a combination of an electrostatic sector and a multipole. The multipoles can comprise a variety of shapes including but not limited to rounded, trapezoidal, triangular, squared, pentagonal, hexagonal, heptagonal, octagonal, enneagonal, or decagonal poles. The ion guide can be bent in a variety of angles from a rounded shape to a triangular shape. The ion guide can be bent at least 60 degrees, 65 degrees, 70 degrees, 75 degrees, 80 degrees, 85 degrees, 90 degrees, 95 degrees, 100 degrees, 105 degrees, 110 degrees, 115 degrees, 120 degrees, 125 degrees, 130 degrees, 135 degrees, 140 degrees, 145 degrees, 150 degrees, 155 degrees, 160 degrees, 165 degrees, 170 degrees, 175 degrees, or 179 degrees. The interdistance between electrodes can also vary. At least two of the distances between electrostatic sectors can be the same.

Figure 8:
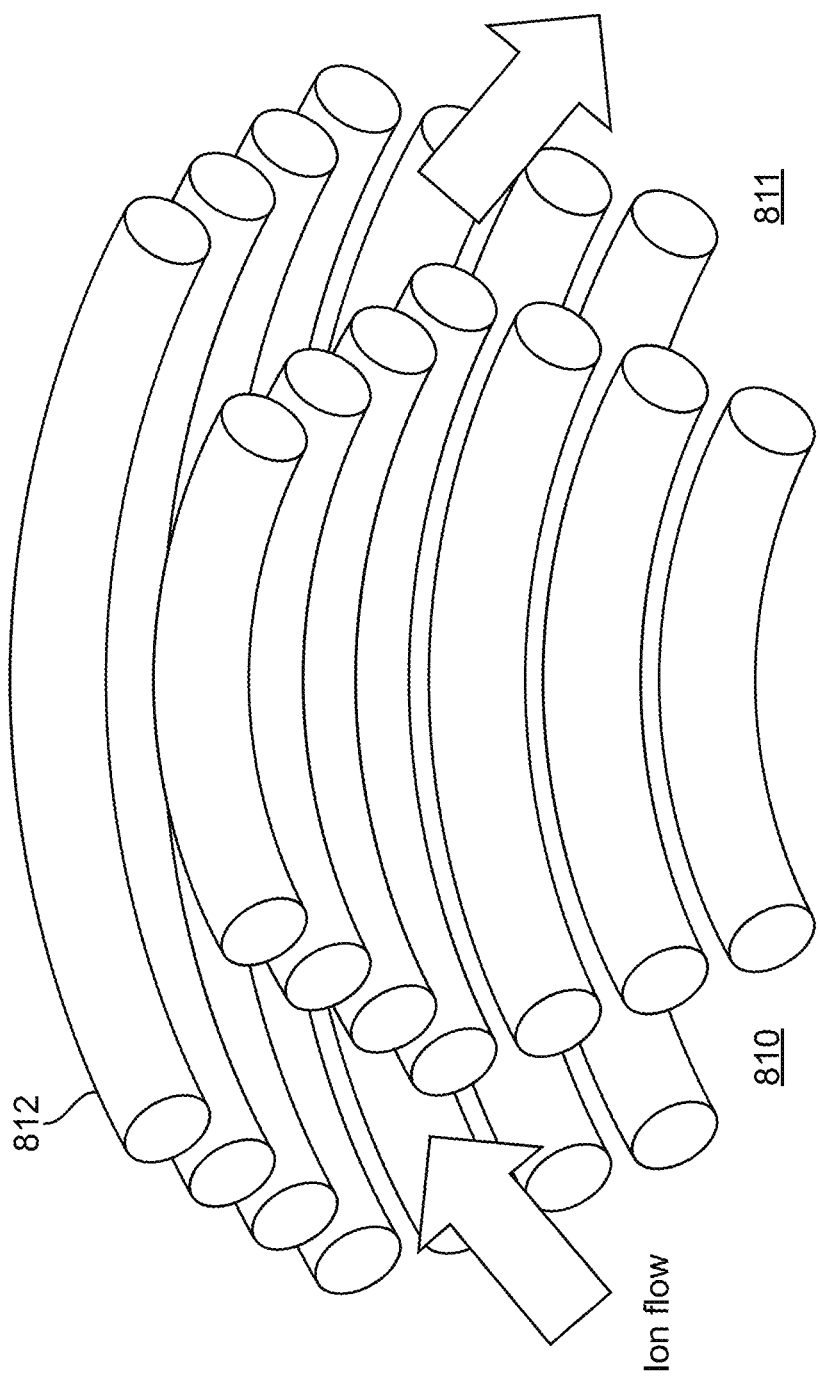
FIG. 8 shows a diagram of a curved ion guide disclosed in the invention by combining electrostatic sectors with a multipole, in accordance with embodiments of the invention.

FIG. 8 shows a plurality of electrostatic sectors which are arranged in parallel along a broken line. The middle pole in each set is offset, creating a V-shaped ion pathway between the poles 812. For each electrostatic sector, a pair of curved electrodes is included, such that there are an equal number of poles in each sector. Two different DC voltages are applied between the two curved electrodes of all electrostatic sectors such that the voltages may alternate between adjacent poles or in the alternative each sector may have a single voltage applied to it. Examples of voltage levels may be provided as any value described elsewhere herein. At the same time, radio frequency (RF) voltages with opposite polarities are separately superimposed on adjacent electrostatic sectors. Examples of voltage levels may be provided as any value described elsewhere herein. This versatility may allow for greater control of the ion path of species within a complex sample of metal isotope tagged single particles.

Figure 9:
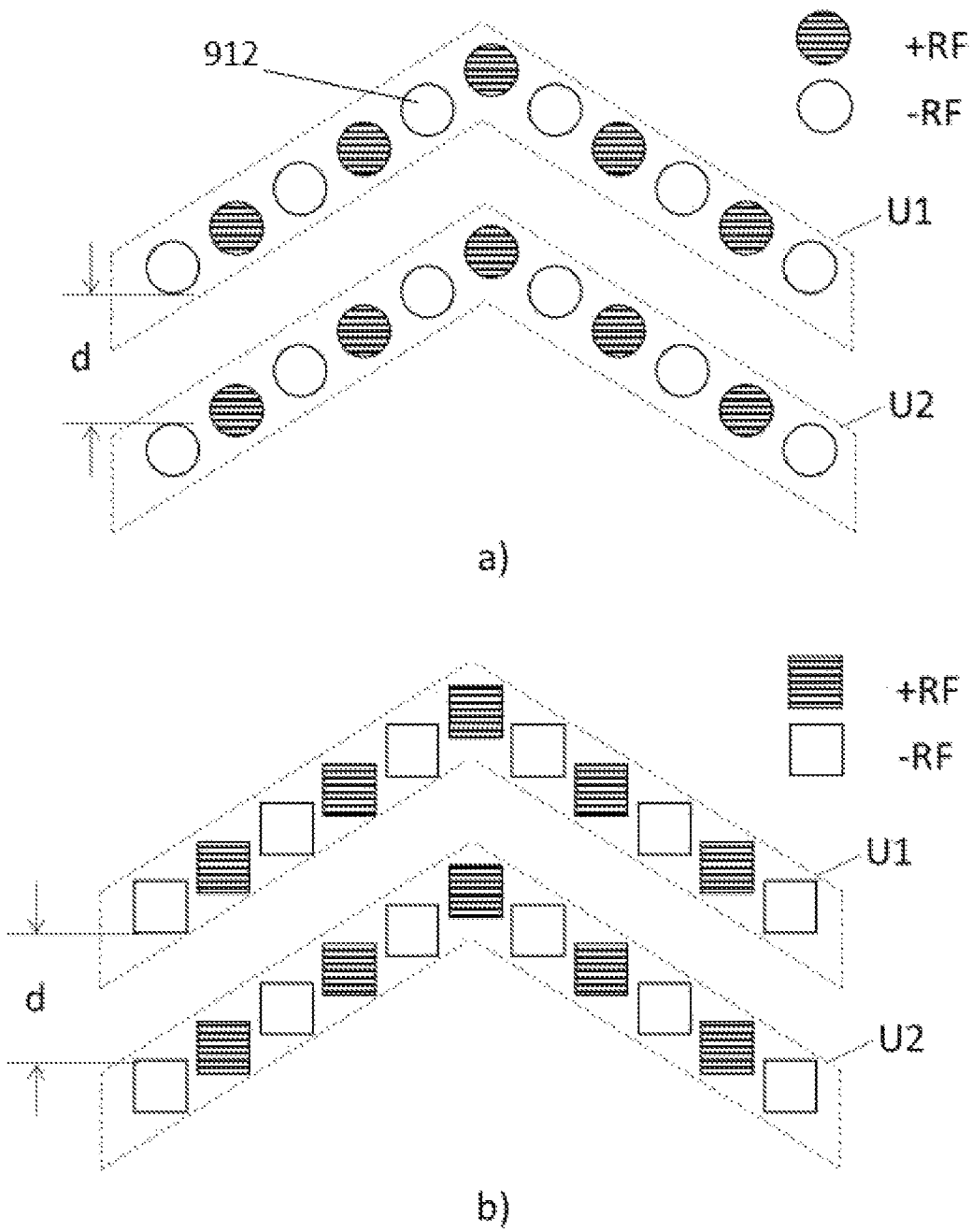
FIG. 9 shows a radial cross section of a curved ion guide wherein an electrostatic sector is combined with a multipole wherein the multipole is constructed with (a) round poles or (b) square poles, in accordance with embodiments of the invention.

FIG. 9 shows a radial cross section of electrostatic sectors with a V-shaped ion pathway between the poles 912 wherein a direct current (DC) and RF voltage has been applied to round poles 912 and square poles 912. Alternatively, the poles can have a variety of cross-sectional shapes including but not limited to rounded, trapezoidal, triangular, squared, pentagonal, hexagonal, heptagonal, octagonal, enneagonal, or decagonal.

Figure 10:
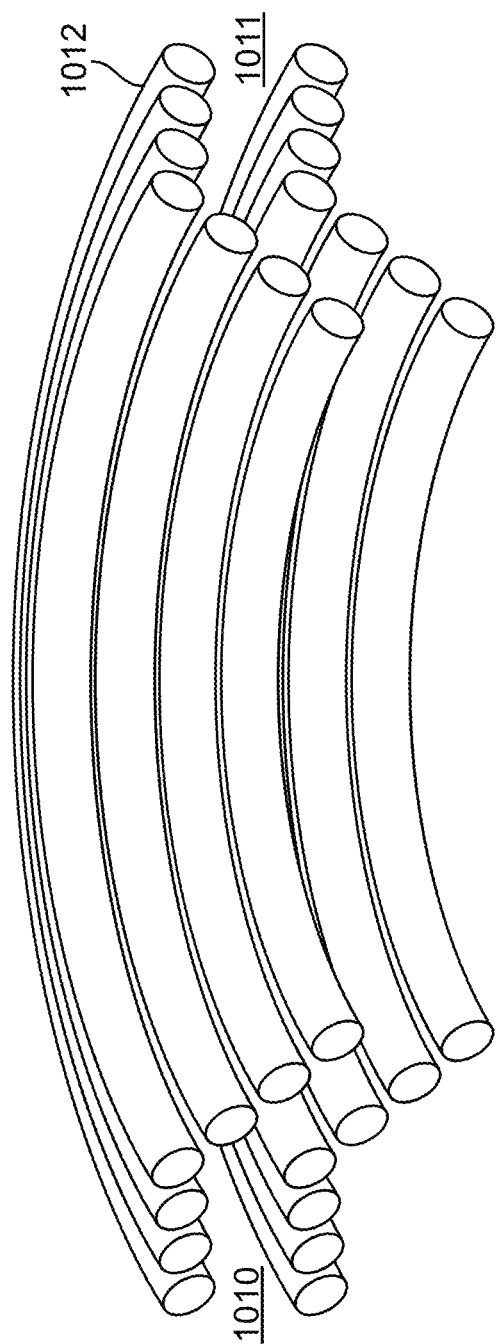
FIG. 10 shows a diagram of a variant of the curved ion guide device wherein the electrostatic sector is combined with a multipole, in accordance with embodiments of the invention.

FIG. 10 shows a variation of the previous embodiment wherein the bending direction is different between sets of poles 1012. The sets of poles have two different DC voltages applied and RF voltages with opposite polarities are superimposed on the adjacent poles of each set. One benefit of the variation disclosed is that the electrodes are not on one plane. In embodiments were the electrodes for each set are placed on one plane, ion deflection and confinement are realized by controlling DC voltages applied on different electrodes requiring many more DC power supplies than the presently disclosed configuration. The more DC power supplies that are required, the more complicated and expensive the setup is. Thus, the presently disclosed configuration is a more effective design in that it is simpler and less expensive than a single plane configuration.

In one embodiment, a first set of poles can be arranged to form a concave profile. The concave profile can comprise a first planar segment and a second planar segment that meets the first planar segment without being parallel to the first planar segment. The concave profile can extend along a length of the first curved section. A second set of poles can be arranged to form a convex profiled. The convex profile can comprise third and fourth planar segments. The fourth planar segment can be placed so as to meet the third planar segment without being parallel to the third planar segment. The convex profile can extend along a length of the second curved section, creating a V-shaped ion channel. Alternatively, or in combination, the concave profile of the first curved section can directly face the convex profile of the second curved section. A length of the concave profile of the first curved section can curve inward. A length of the convex profile of the second curved section can curve outward. Alternatively, or in combination, a length of the concave profile of the first curved section can curve laterally. A length of the convex profile of the second curved section can curve laterally in the same direction.

Figure 11:
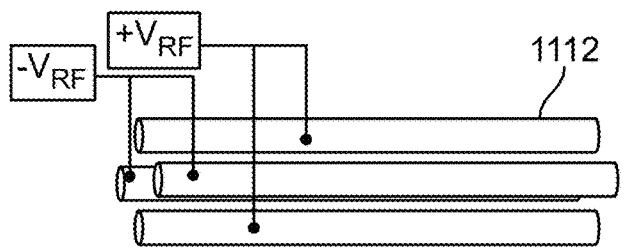
FIG. 11 shows a comparison of quadrupole devices for removing interference ions (a and b) and ion manipulation devices to filter arbitrary ions based on quadrupole and SWIFT voltage technology (c, d, and e), in accordance with embodiments of the invention.
Figure 11:
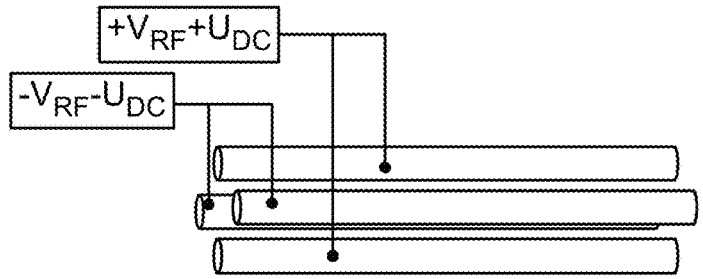
Figure 11:
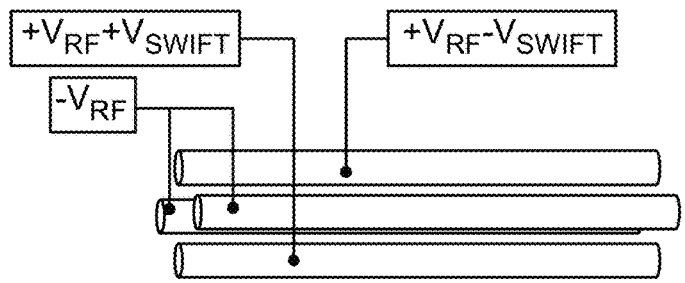
Figure 11:
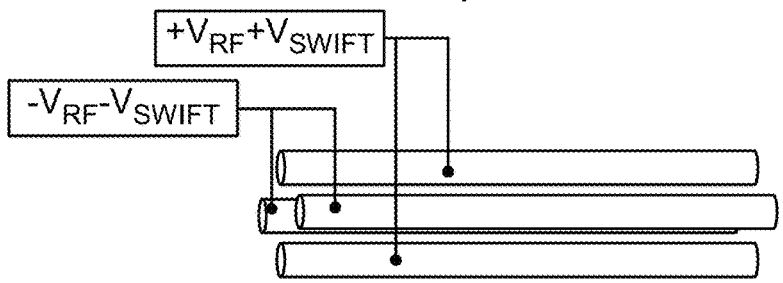
Figure 11:
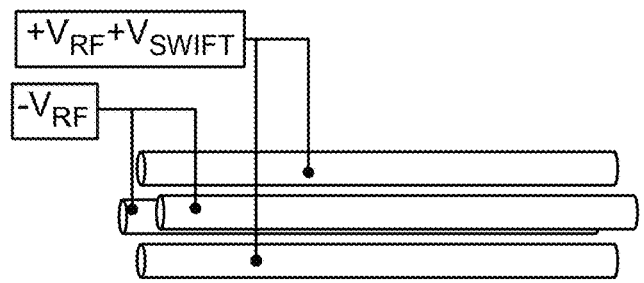

FIG. 11 shows an ion manipulation device combining quadrupole 1112 and stored-waveform inverse Fourier transform (SWIFT) technology. SWIFT technology is a method used in fourier-transform ion cyclotron resonance (FTICR) mass spectrometry and ion trap mass spectrometry for isolating specific ions. By using such a combination, the ion manipulation device can selectively remove ions with arbitrary mass without effecting the transmission of targeted ions. Thus, the above-mentioned deficiencies existing in the prior—can be solved. The ion manipulation structure and three possible application methods of SWIFT voltage are shown in panels c, d, and e. One method of applying SWIFT voltages with opposite polarities on a pair of electrodes of the quadrupole is shown in panel c. Alternatively, the SWIFT voltages with opposite polarities can be superimposed on the two pairs of electrodes of quadrupole as shown in panel d. Furthermore, one SWIFT voltage can be applied to only one pair of electrodes of the quadrupole as shown in panel e.

In one embodiment, the voltage applied to a first set of poles can include an RF voltage plus a SWIFT voltage. The voltages applied to the second set of poles can include a minus RF voltage. Alternatively, the voltages applied to the second set of poles can include a minus RF voltage minus a SWIFT voltage. In another embodiment, a first voltage applied to a first pole within the first set of poles includes an RF voltage plus a SWIFT voltage. A second voltage applied to a second pole within the first set of poles can include a RF voltage minus a SWIFT voltage. Alternatively, or in combination, voltages applied to the second set of poles can include a minus RF voltage.

The peak-to-peak amplitude of RF voltage may be from 0 volts (V) to 100V, 100V to 200V, 200V to 300V, 300V to 400V, 400V to 500V, 500V to 600V, 600V to 700V, 700V to 800 V, 800V to 900V, 900V to 1000V, 1000V to 1100V, 1100V to 1200V, 1200V to 1300V, 1300V to 1400V, 1400V to 1500V, 1500V to 1600V, 1600V to 1700V, 1700V to 1800 V, 1800V to 1900V, 1900V to 2000V, 2000V to 2100V, 2100V to 2200V, 2200V to 2300V, 2300V to 2400V, 2400V to 2500V, 2500V to 2600V, 2600V to 2700V, 2700V to 2800 V, 2800V to 2900V, 2900V to 3000V, 3000V to 3100V, 3100V to 3200V, 3200V to 3300V, 3300V to 3400V, 3400V to 3500V, 3500V to 3600V, 3600V to 3700V, 3700V to 3800 V, 3800V to 3900V, 3900V to 4000V, 4000V to 4100V, 4100V to 4200V, 4200V to 4300V, 4300V to 4400V, 4400V to 4500V, 4500V to 4600V, 4600V to 4700V, 4700V to 4800 V, 4800V to 4900V, or 4900V to 5000V. The peak-to-peak amplitude of RF voltage may be greater than about 0V, 100V, 200V, 300V, 400V, 500V, 600V, 700V, 800 V, 800V, 900V, 1000V, 1100V, 1200V, 1300V, 1400V, 1500V, 1600V, 1700V, 1800 V, 1900V, 2000V, 2100V, 2200V, 2300V, 2400V, 2500V, 2600V, 2700V, 2800 V, 2900V, 3000V, 3100V, 3200V, 3300V, 3400V, 3500V, 3600V, 3700V, 3800 V, 3900V, 4000V, 4100V, 4200V, 4300V, 4400V, 4500V, 4600V, 4700V, 4800 V, 4900V, or 5000V. The peak-to-peak amplitude of RF voltage may be less than about 5000V, 4900V, 4800V, 4700V, 4600V, 4500V, 4400V, 4300V, 4200V, 4100V, 4000V, 3900V, 3800V, 3700V, 3600V, 3500V, 3400V, 3300V, 3200V, 3100V, 3000V, 2900V, 2800V, 2700V, 2600V, 2500V, 2400V, 2300V, 2200V, 2100V, 2000V, 1900V, 1800V, 1700V, 1600V, 1500V, 1400V, 1300V, 1200V, 1100V, 1000V, 900V, 800V, 700V, 600V, 500V, 400V, 300V, 200V, 100V, or 10V. The peak-to-peak amplitude of RF voltage may be between any values provided above.

The frequency of RF voltage may be from 100 kilohertz (kHz) to 1 megahertz (MHz), 1 MHz to 2 MHz, 2 MHz to 3 MHz, 3 MHz to 4 MHz, 4 MHz to 5 MHz, 5 MHz to 6 MHz, 6 MHz to 7 MHz, 7 MHz to 8 MHz, 8 MHz to 9 MHz, 9 MHz to 10 MHz, 10 MHz to 11 MHz, 11 MHz to 12 MHz, 12 MHz to 13 MHz, 13 MHz to 14 MHz, 14 MHz to 15 MHz, 15 MHz to 16 MHz, 16 MHz to 17 MHz, 17 MHz to 18 MHz, 18 MHz to 19 MHz, 19 MHz to 20 MHz, 20 MHz to 21 MHz, 21 MHz to 22 MHz, 22 MHz to 23 MHz, 23 MHz to 24 MHz, 24 MHz to 25 MHz, 25 MHz to 26 MHz, 26 MHz to 27 MHz, 27 MHz to 28 MHz, 28 MHz to 29 MHz, 29 MHz to 30 MHz, 30 MHz to 31 MHz, 31 MHz to 32 MHz, 32 MHz to 33 MHz, 33 MHz to 34 MHz, 34 MHz to 35 MHz, 35 MHz to 36 MHz, 36 MHz to 37 MHz, 37 MHz to 38 MHz, 38 MHz to 39 MHz, 39 MHz to 40 MHz, 40 MHz to 41 MHz, 41 MHz to 42 MHz, 42 MHz to 43 MHz, 43 MHz to 44 MHz, 44 MHz to 45 MHz, 45 MHz to 46 MHz, 46 MHz to 47 MHz, 47 MHz to 48 MHz, 48 MHz to 49 MHz, or 49 MHz to 50 MHz. The frequency of RF voltage may be greater than about 100 kilohertz (kHz), 1 megahertz (MHz), 2 MHz, 3 MHz, 4 MHz, 5 MHz, 6 MHz, 7 MHz, 8 MHz, 9 MHz, 10 MHz, 11 MHz, 12 MHz, 13 MHz, 14 MHz, 15 MHz, 16 MHz, 17 MHz, 18 MHz, 19 MHz, 20 MHz, 21 MHz, 22 MHz, 23 MHz, 24 MHz, 25 MHz, 26 MHz, 27 MHz, 28 MHz, 29 MHz, 30 MHz, 31 MHz, 32 MHz, 33 MHz, 34 MHz, 35 MHz, 36 MHz, 37 MHz, 38 MHz, 39 MHz, 40 MHz, 41 MHz, 42 MHz, 43 MHz, 44 MHz, 45 MHz, 46 MHz, 47 MHz, 48 MHz, 49 MHz, or 50 MHz. The frequency of RF voltage may be less than about 50 MHz, 49 MHz, 48 MHz, 47 MHz, 46 MHz, 45 MHz, 44 MHz, 43 MHz, 42 MHz, 41 MHz, 40 MHz, 39 MHz, 38 MHz, 37 MHz, 36 MHz, 35 MHz, 34 MHz, 33 MHz, 32 MHz, 31 MHz, 30 MHz, 29 MHz, 28 MHz, 27 MHz, 26 MHz, 25 MHz, 24 MHz, 23 MHz, 22 MHz, 21 MHz, 20 MHz, 19 MHz, 18 MHz, 17 MHz, 16 MHz, 15

MHz, 14 MHz, 13 MHz, 12 MHz, 11 MHz, 10 MHz, 9 MHz, 8 MHz, 7 MHz, 6 MHz, 5 MHz, 4 MHz, 3 MHz, 2 MHz, 1 MHz, or 100 kHz. The frequency of RF voltage may be between any values provided above.

The amplitude of SWIFT voltage may be from 0 volts (V) to 10V, 10V to 20V, 20V to 30V, 30V to 40V, 40V to 50V, 50V to 60V, 60V to 70V, 70V to 80V, 80V to 90V, 90V to 100V. The amplitude of SWIFT voltage may be greater than about 10V, 20V, 30V, 40V, 50V, 60V, 70V, 80V, 90V, or 100V. The amplitude of SWIFT voltage may be less than about 100V, 90V, 80V, 70V, 60V, 50V, 40V, 30V, 20V, or 10V. The amplitude of SWIFT voltage may be between any values provided above.

The frequency components may be from 10 kilohertz (kHz) to 1 megahertz (MHz), 1 MHz to 2 MHz, 2 MHz to 3 MHz, 3 MHz to 4 MHz, 4 MHz to 5 MHz, 5 MHz to 6 MHz, 6 MHz to 7 MHz, 7 MHz to 8 MHz, 8 MHz to 9 MHz, 9 MHz to 10 MHz, 10 MHz to 11 MHz, 11 MHz to 12 MHz, 12 MHz to 13 MHz, 13 MHz to 14 MHz, 14 MHz to 15 MHz, 15 MHz to 16 MHz, 16 MHz to 17 MHz, 17 MHz to 18 MHz, 18 MHz to 19 MHz, 19 MHz to 20 MHz, 20 MHz to 21 MHz, 21 MHz to 22 MHz, 22 MHz to 23 MHz, 23 MHz to 24 MHz, 24 MHz to 25 MHz, 25 MHz to 26 MHz, 26 MHz to 27 MHz, 27 MHz to 28 MHz, 28 MHz to 29 MHz, 29 MHz to 30 MHz, 30 MHz to 31 MHz, 31 MHz to 32 MHz, 32 MHz to 33 MHz, 33 MHz to 34 MHz, 34 MHz to 35 MHz, 35 MHz to 36 MHz, 36 MHz to 37 MHz, 37 MHz to 38 MHz, 38 MHz to 39 MHz, 39 MHz to 40 MHz, 40 MHz to 41 MHz, 41 MHz to 42 MHz, 42 MHz to 43 MHz, 43 MHz to 44 MHz, 44 MHz to 45 MHz, 45 MHz to 46 MHz, 46 MHz to 47 MHz, 47 MHz to 48 MHz, 48 MHz to 49 MHz, 49 MHz to 50 MHz. The frequency components may be greater than about 100 kilohertz (kHz), 1 megahertz (MHz), 2 MHz, 3 MHz, 4 MHz, 5 MHz, 6 MHz, 7 MHz, 8 MHz, 9 MHz, 10 MHz, 11 MHz, 12 MHz, 13 MHz, 14 MHz, 15 MHz, 16 MHz, 17 MHz, 18 MHz, 19 MHz, 20 MHz, 21 MHz, 22 MHz, 23 MHz, 24 MHz, 25 MHz, 26 MHz, 27 MHz, 28 MHz, 29 MHz, 30 MHz, 31 MHz, 32 MHz, 33 MHz, 34 MHz, 35 MHz, 36 MHz, 37 MHz, 38 MHz, 39 MHz, 40 MHz, 41 MHz, 42 MHz, 43 MHz, 44 MHz, 45 MHz, 46 MHz, 47 MHz, 48 MHz, 49 MHz, or 50 MHz. The frequency of components may be less than about 50 MHz, 49 MHz, 48 MHz, 47 MHz, 46 MHz, 45 MHz, 44 MHz, 43 MHz, 42 MHz, 41 MHz, 40 MHz, 39 MHz, 38 MHz, 37 MHz, 36 MHz, 35 MHz, 34 MHz, 33 MHz, 32 MHz, 31 MHz, 30 MHz, 29 MHz, 28 MHz, 27 MHz, 26 MHz, 25 MHz, 24 MHz, 23 MHz, 22 MHz, 21 MHz, 20 MHz, 19 MHz, 18 MHz, 17 MHz, 16 MHz, 15 MHz, 14 MHz, 13 MHz, 12 MHz, 11 MHz, 10 MHz, 9 MHz, 8 MHz, 7 MHz, 6 MHz, 5 MHz, 4 MHz, 3 MHz, 2 MHz, 1 MHz, or 100 kHz. The frequency of components may be between any values provided above.

Figure 12:
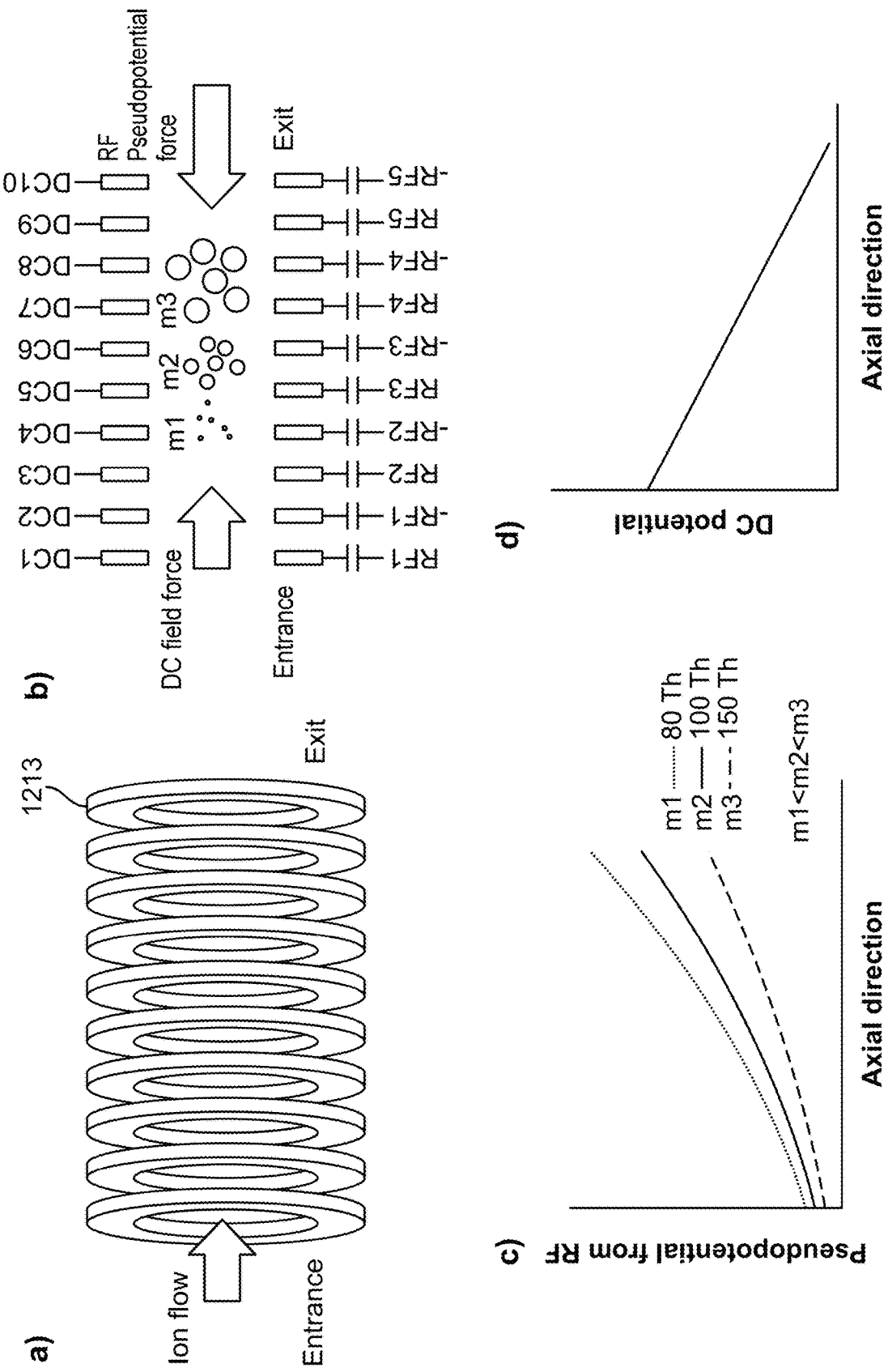
FIG. 12 shows an ion manipulation device based on ion tunnel, in accordance with embodiments of the invention.

FIG. 12 shows an ion manipulation device comprising an ion tunnel device. An ion tunnel device can comprise a plurality of stacked right electrodes 1213 as shown in panel a. RF voltages with opposite polarities can be applied between adjacent ring electrodes. The RF voltages can be used to confine ions in the radial direction. Different DC voltages, for example as in panel b, can be separately applied to each of the ring electrodes for controlling the ion movement in the axial direction. However, the present disclosure provides for the application of RF voltages of different amplitudes so as to form a RF potential gradient in the axial direction.

The peak-to-peak amplitude of RF voltage may be from 0 volts (V) to 100V, 100V to 200V, 200V to 300V, 300V to 400V, 400V to 500V, 500V to 600V, 600V to 700V, 700V to 800 V, 800V, to 900V, 900V, to 1000V, 1000V to 1100V, 1100V to 1200V, 1200V to 1300V, 1300V to 1400V, 1400V to 1500V, 1500V to 1600V, 1600V to 1700V, 1700V to 1800 V, 1800V3 to 1900V, 1900V to 2000V, 2000V to 2100V, 2100V to 2200V, 2200V to 2300V, 2300V to 2400V, 2400V to 2500V, 2500V to 2600V, 2600V to 2700V, 2700V to 2800 V, 2800V to 2900V, 2900V to 3000V, 3000V to 3100V, 3100V to 3200V, 3200V to 3300V, 3300V to 3400V, 3400V to 3500V, 3500V to 3600V, 3600V to 3700V, 3700V to 3800 V, 3800V to 3900V, 3900V to 4000V, 4000V to 4100V, 4100V to 4200V, 4200V to 4300V, 4300V to 4400V, 4400V to 4500V, 4500V to 4600V, 4600V to 4700V, 4700V to 4800 V, 4800V to 4900V, 4900V to 5000V. The peak-to-peak amplitude of RF voltage may be greater than about 0V, 100V, 200V, 300V, 400V, 500V, 600V, 700V, 800 V, 800V, 900V, 1000V, 1100V, 1200V, 1300V, 1400V, 1500V, 1600V, 1700V, 1800 V, 1900V, 2000V, 2100V, 2200V, 2300V, 2400V, 2500V, 2600V, 2700V, 2800 V, 2900V, 3000V, 3100V, 3200V, 3300V, 3400V, 3500V, 3600V, 3700V, 3800 V, 3900V, 4000V, 4100V, 4200V, 4300V, 4400V, 4500V, 4600V, 4700V, 4800 V, 4900V, or 5000V. The peak-to-peak amplitude of RF voltage may be less than about 5000V, 4900V, 4800V, 4700V, 4600V, 4500V, 4400V, 4300V, 4200V, 4100V, 4000V, 3900V, 3800V, 3700V, 3600V, 3500V, 3400V, 3300V, 3200V, 3100V, 3000V, 2900V, 2800V, 2700V, 2600V, 2500V, 2400V, 2300V, 2200V, 2100V, 2000V, 1900V, 1800V, 1700V, 1600V, 1500V, 1400V, 1300V, 1200V, 1100V, 1000V, 900V, 800V, 700V, 600V, 500V, 400V, 300V, 200V, 100V, or 10V. The peak-to-peak amplitude of RF voltage may be between any values provided above.

The frequency of RF voltage may be from 100 kilohertz (kHz) to 1megahertz (MHz), 1 MHz to 2 MHz, 2 MHz to 3 MHz, 3 MHz to 4 MHz, 4 MHz to 5 MHz, 5 MHz to 6 MHz, 6 MHz to 7 MHz, 7 MHz to 8 MHz, 8 MHz to 9 MHz, 9 MHz to 10 MHz, 10 MHz to 11 MHz, 11 MHz to 12 MHz, 12 MHz to 13 MHz, 13 MHz to 14 MHz, 14 MHz to 15 MHz, 15 MHz to 16 MHz, 16 MHz to 17 MHz, 17 MHz to 18 MHz, 18 MHz to 19 MHz, 19 MHz to 20 MHz, 20 MHz to 21 MHz, 21 MHz to 22 MHz, 22 MHz to 23 MHz, 23 MHz to 24 MHz, 24 MHz to 25 MHz, 25 MHz to 26 MHz, 26 MHz to 27 MHz, 27 MHz to 28 MHz, 28 MHz to 29 MHz, 29 MHz to 30 MHz, 30 MHz to 31 MHz, 31 MHz to 32 MHz, 32 MHz to 33 MHz, 33 MHz to 34 MHz, 34 MHz to 35 MHz, 35 MHz to 36 MHz, 36 MHz to 37 MHz, 37 MHz to 38 MHz, 38 MHz to 39 MHz, 39 MHz to 40 MHz, 40 MHz to 41 MHz, 41 MHz to 42 MHz, 42 MHz to 43 MHz, 43 MHz to 44 MHz, 44 MHz to 45 MHz, 45 MHz to 46 MHz, 46 MHz to 47 MHz, 47 MHz to 48 MHz, 48 MHz to 49 MHz, or 49 MHz to 50 MHz. The frequency of RF voltage may be greater than about 100 kilohertz (kHz), 1 megahertz (MHz), 2 MHz, 3 MHz, 4 MHz, 5 MHz, 6 MHz, 7 MHz, 8 MHz, 9 MHz, 10 MHz, 11 MHz, 12 MHz, 13 MHz, 14 MHz, 15 MHz, 16 MHz, 17 MHz, 18 MHz, 19 MHz, 20 MHz, 21 MHz, 22 MHz, 23 MHz, 24 MHz, 25 MHz, 26 MHz, 27 MHz, 28 MHz, 29 MHz, 30 MHz, 31 MHz, 32 MHz, 33 MHz, 34 MHz, 35 MHz, 36 MHz, 37 MHz, 38 MHz, 39 MHz, 40 MHz, 41 MHz, 42 MHz, 43 MHz, 44 MHz, 45 MHz, 46 MHz, 47 MHz, 48 MHz, 49 MHz, or 50 MHz. The frequency of RF voltage may be less than about 50 MHz, 49 MHz, 48 MHz, 47 MHz, 46 MHz, 45 MHz, 44 MHz, 43 MHz, 42 MHz, 41 MHz, 40 MHz, 39 MHz, 38 MHz, 37 MHz, 36 MHz, 35 MHz, 34 MHz, 33 MHz, 32 MHz, 31 MHz, 30 MHz, 29 MHz, 28 MHz, 27 MHz, 26 MHz, 25 MHz, 24 MHz, 23 MHz, 22 MHz, 21 MHz, 20 MHz, 19 MHz, 18 MHz, 17 MHz, 16 MHz, 15 MHz, 14 MHz, 13 MHz, 12 MHz, 11 MHz, 10 MHz, 9 MHz, 8 MHz, 7 MHz, 6 MHz, 5 MHz, 4 MHz, 3 MHz, 2 MHz, 1 MHz, or 100 kHz. The frequency of RF voltage may be between any values provided above.

The RF potential gradient can impose opposite force on ions against that from the DC potential gradient. According to the pseudopotential theory of RF multipolar field, the effective potential for ions with different masses will also be different. This is illustrated in panel c. Concurrently, the potential gradient generated by the DC voltages imposes an equal force on all ions independent of the mass of the ion, as show in panel d. The present disclosure therefore adjusts the force generated by the DC voltage and the force generated by the RF potential gradient to change the motion state of ions with different m/z values, in the axial direction. For example, when the two opposing forces generated by the DC voltage and the RF potential gradient act on a group of ions equal in magnitude, the ion will lose its axial driving force and stay suspended at an axial point, moving back and forth in the radial direction. However, under the same situation another group of ions with varying mass can be driven forward or pushed backward in the axial direction. Therefore, described in the present disclosure is a mechanism by which mass filtration, ion storage and rough mass separation can be realized.

Panel B shows an embodiment wherein the amplitude of RF voltages is gradually increased and the DC voltages are gradually decreased from entrance to exit. Thus, ions stay at different locations along the axial axis by mass order and high mass ions are nearer to the exit. Concurrently, ions with a mass lower than a certain mass will be forced backward by net force. This net force can keep the ions with a mass lower than the certain mass from entering the manipulation device. The net force can also push ions with a mass higher than the certain mass out of the ion manipulation device. The presently disclosed net force and its uses offer advantages such an improved duty cycle and sensitivity in that the net force will drive high mass ions with a higher ejection energy than low mass ions with a lower energy. Alternatively or in combination, by controlling the RF voltages and DC voltages over time, the ions can be first stored, separated axially, and then released in order of descending mass value. Alternatively or in combination, other mechanisms for removing ions can be used to remove ions, such as interference ions.

Figure 13:
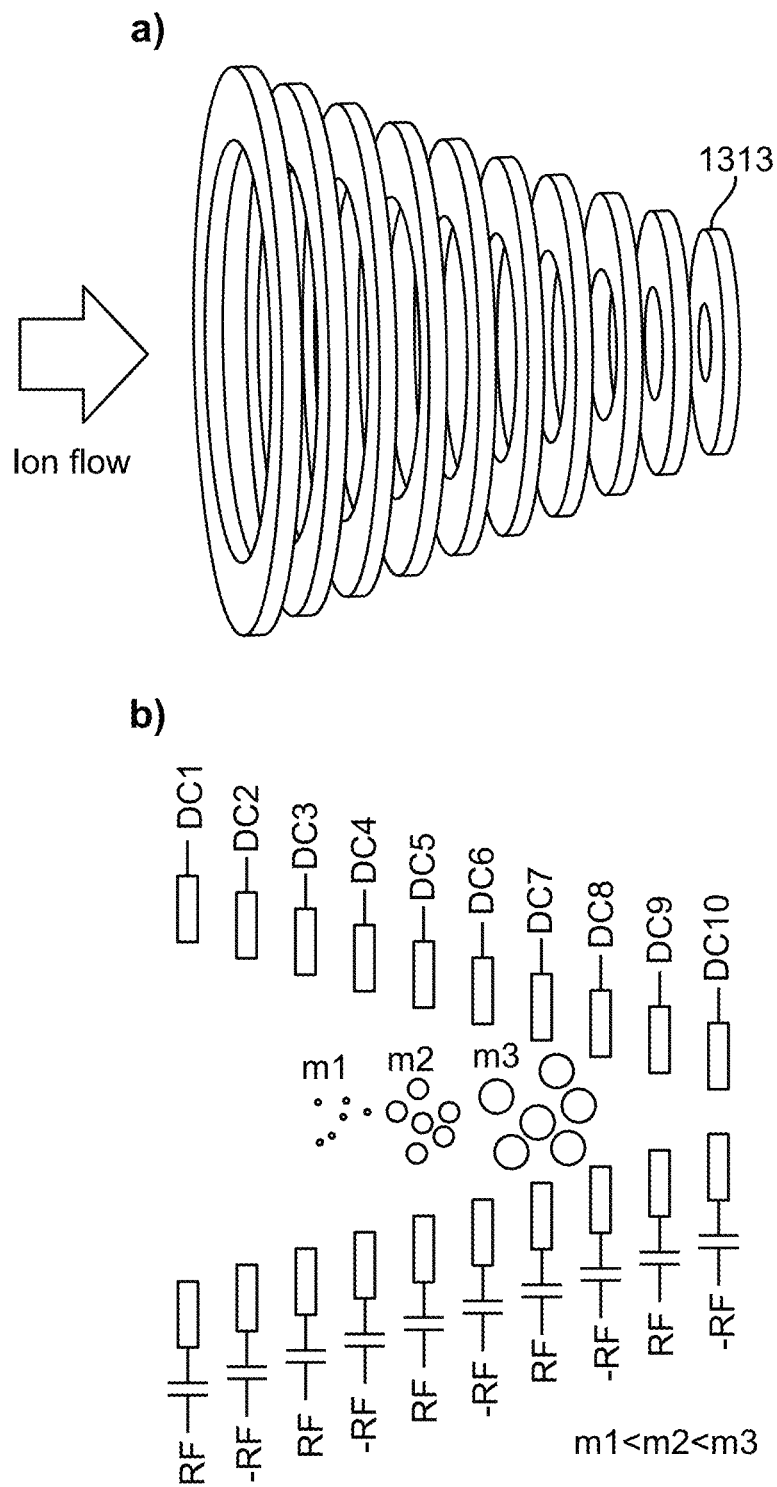
FIG. 13 shows an ion manipulation device based on ion funnel, in accordance with embodiments of the invention.

FIG. 13 shows an ion manipulation device based on an ion funnel 1313 wherein the inner diameter of each ring electrode is gradually changed. A RF pseudopotential gradient in the axial direction can also be formed. This can reduce the system complexity and cost in that the amplitude of the RF voltage used can be constant. Alternatively, or in combination, the axial space and thickness of each ring electrode can be adjusted to achieve a similar purpose.

In one embodiment, the ion manipulation device comprises a plurality of stacked ring electrodes to form a tunnel wherein ion enter at one end and exit at another end. RF voltages of opposite polarities can be applied to adjacent ring electrodes. DC voltages can be applied separated to each ring electrode to control ion movement in an axial direction through the ring electrodes. The amplitude of the RF voltages applied can be gradually increased from entrance to exit, or it can be substantially constant from the entrance to the exit. Additionally, the amplitude of the DC voltages applied to the ring electrodes can be gradually decreased from entrance to exit or it can be substantially constant from the entrance to the exit. The axial space between each ring electrode can be substantially the same or it can change along the length of the tunnel, or any combination thereof. The thickness of each ring electrode can be substantially the same, or it can change along the length of the tunnel, or any combination thereof.

Figure 14:
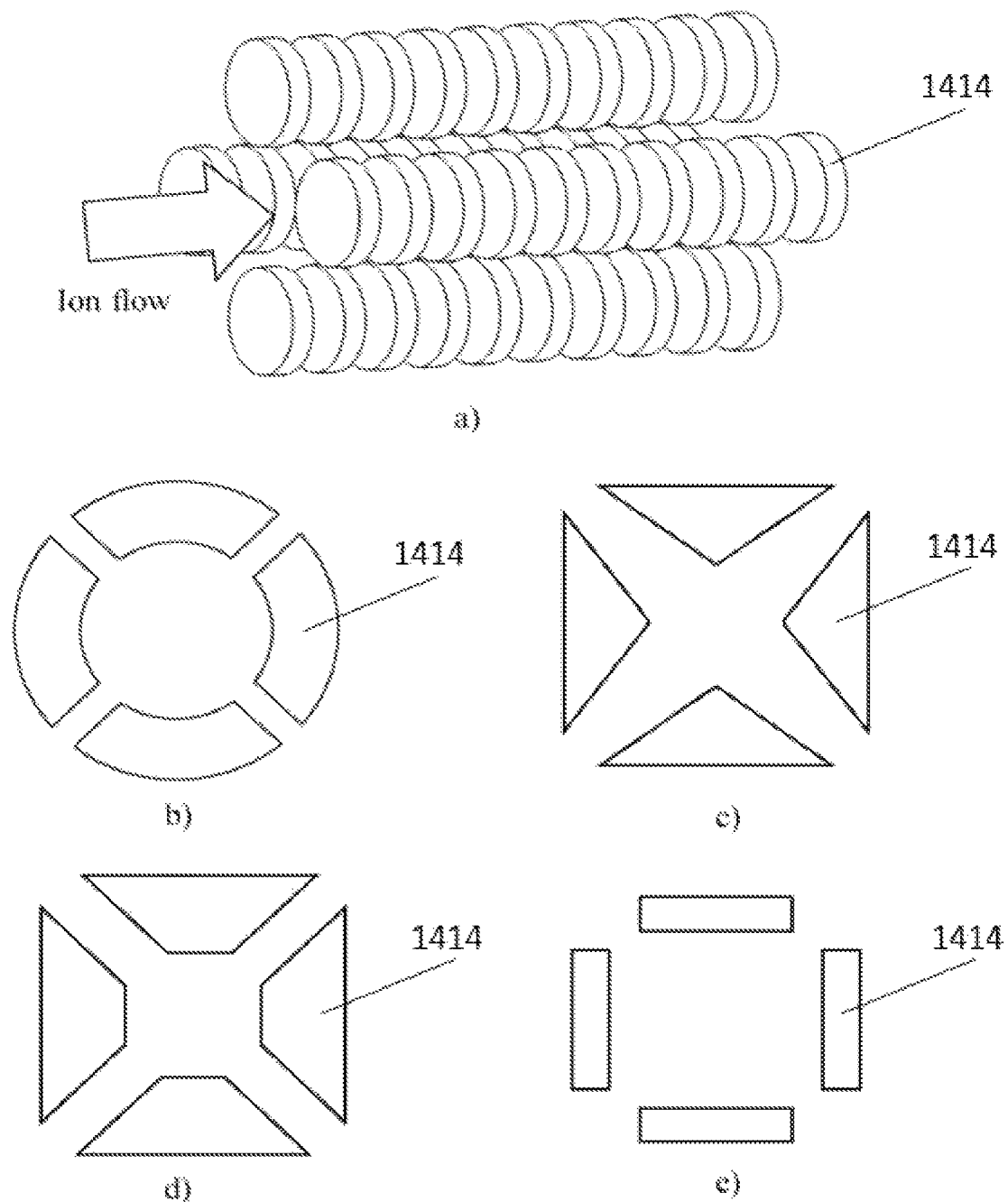
FIG. 14 shows an ion manipulation device based on axially segmented quadrupole wherein (a) is a segmented quadrupole device using electrodes with a round cross section; (b) uses electrodes with a fan shape; (c) uses electrodes with a triangle shape; (d) uses electrodes with a trapezoid shape; (e) uses electrodes with square cross sections, in accordance with embodiments of the invention.

FIG. 14 shows an ion manipulation device can comprise an axially segmented quadrupole or multipole. The RF voltage can be applied in a similar manner to the quadrupole and multipoles described above. RF voltages with opposite polarities can be applied on adjacent electrodes in each quadrupole/multipole segment. Concurrently, DC voltages can be applied to each segment to generate a DC potential gradient in the axial direction. Alternatively, the amplitude of RF voltages applied on different segments can be varied to generate a RF pseudopotential gradient in the axial direction. Alternatively, or in combination, SWIFT voltages can be superimposed on the segmented quadrupole to provide a mechanism by which interference ions can be removed. As shown, the cross sections of electrodes of the segmented quadrupole can be of any shape, including but not limited to a circular shape, a fan shape, a triangle shape, a trapezoidal shape, or a rectangular shape.

Presently disclosed is an ion manipulation device, a single RF quadrupole, to improve the duty ratio of a TOF mass analyzer. The structure can be a quadrupole comprising four rod electrodes placed in parallel. Each opposing rod pair can be connected electrically. A RF voltage and a DC voltage can be applied to one rod pair. A DC voltage can be applied to the other rod pair. Two endcap electrodes can be applied carrying DC voltages at opposite ends of the single RF quadrupole. The axial electric field generated can be changed in two regions between the endcap electrodes and the single RF quadrupole. Upon application of specific DC voltages and RF voltage, the direction of the axial electric field in the region will also change. The frequency of change is related to the frequency of RF voltage. As a continuous flow of ions fly through the region, the periodically varying electric field can act as an ion gate, dividing the continuous ion flow into separate ion packets. By controlling the frequency of the RF and the amplitude of the RF or DC voltages, the open time and the interval time of the ion gate can be adjusted to control the time length and time interval of adjacent ion packets.

Figure 15:
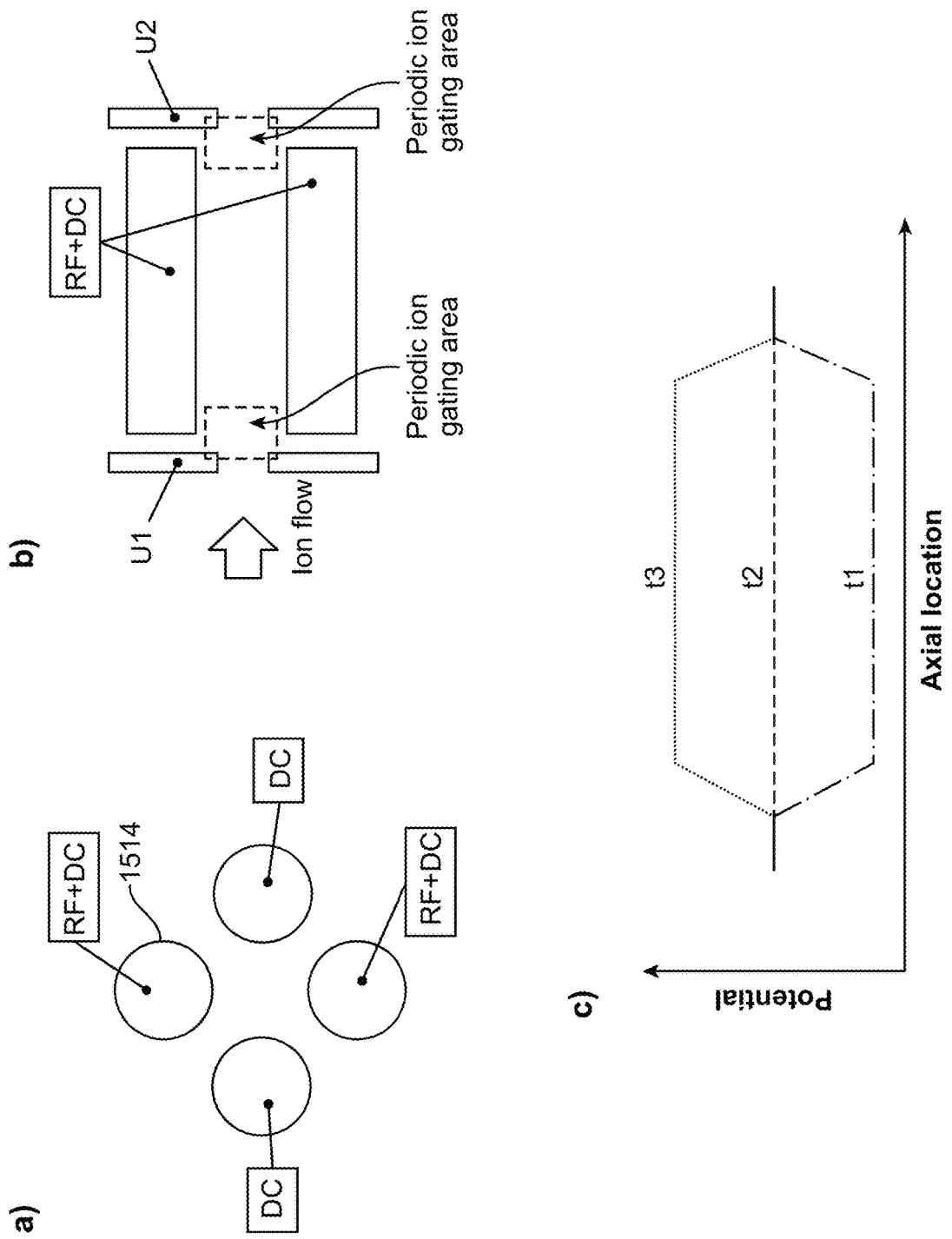
FIG. 15 shows an ion manipulation device based on single RF quadrupole for increasing duty cycle of TOF mass analyzer, in accordance with embodiments of the invention.

FIG. 15 shows the time sequence of two equivalent ion gates generated from a single RF quadrupole ion manipulation device. Controlling the open time interval of the two ion gates in order to match the time flight of ions between the two ion gates results in ion axial compression. The time interval may be about 5 microseconds (µs) to 100 µs, 100 µs to 200 µs, 200 µs to 300 µs, 300 µs to 400 µs, 400 µs to 500 µs, 500 µs to 600 µs, 600 µs to 700 µs, 700 µs to 800 µs, 800 µs to 900 µs, 900 µs to 1 millisecond (ms), 1 ms to 2 ms, 2 ms to 3 ms, 3 ms to 4 ms, 4 ms to 5 ms. The time interval may be greater than about 5 microseconds (µs), 100 µs, 200 µs, 300 µs, 400 µs, 500 µs, 600 µs, 700 µs, 800 µs, 900 µs, 1 millisecond (ms), 2 ms, 3 ms, 4 ms, or 5 ms. The time interval may be less than about 5 ms, 4 ms, 3 ms, 2 ms, 1 ms, 900 µs, 800 µs, 700 µs, 600 µs, 500 µs, 400 µs, 300 µs, 200 µs, 100 µs, or 5 µs. The time interval may be between any values provided above. Ion axial compression effectively decreases the time length of an ion packet.

Figure 16:
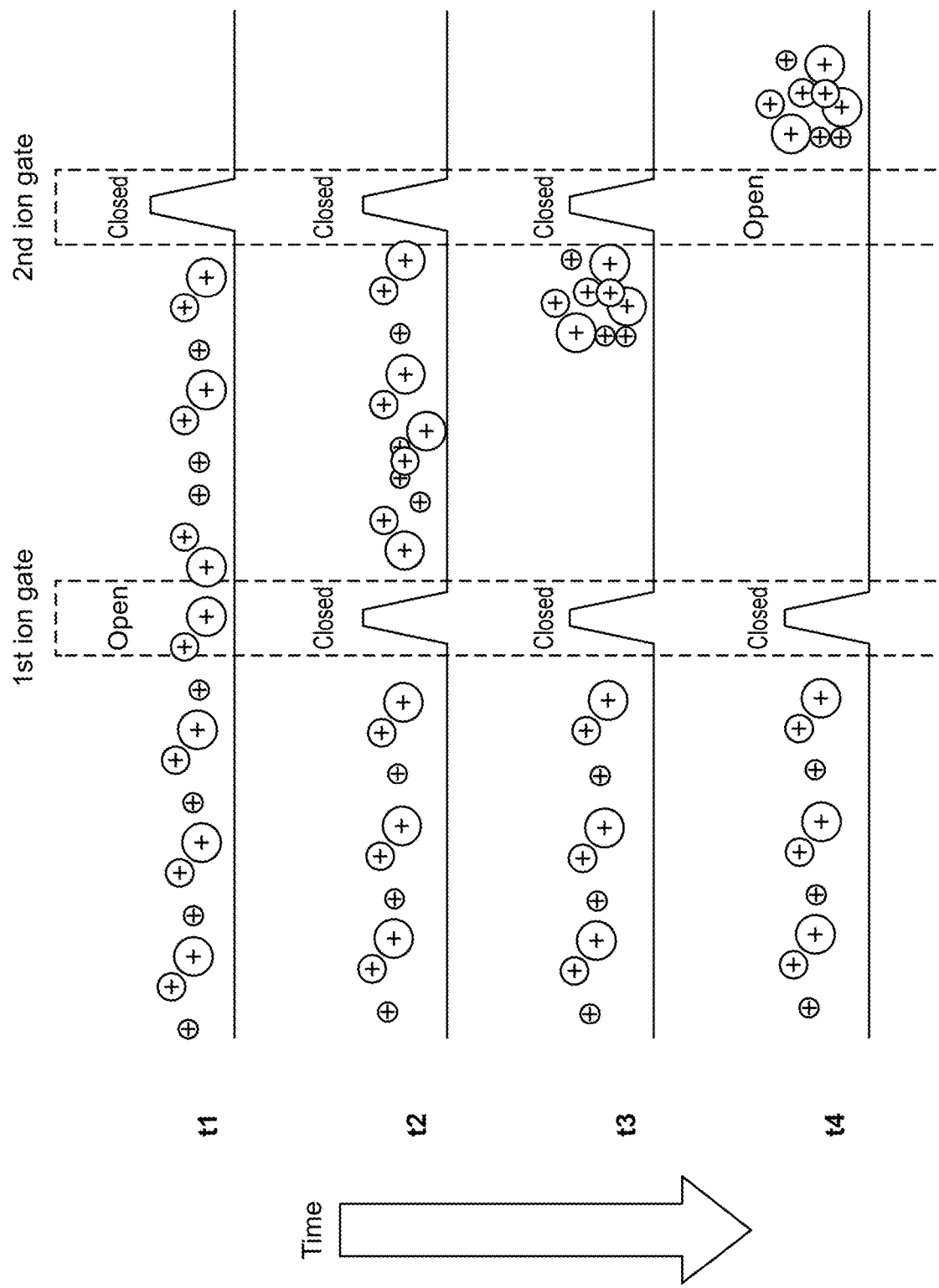
FIG. 16 shows a time sequence of two equivalent ion gates generated from ion manipulation device based on single RF quadrupole for increasing duty cycle of TOF mass analyzer, in accordance with embodiments of the invention.

FIG. 16 shows an operation time sequence. At time t1, ion gate 1 is open and ion gate 2 is closed. The continuous ion flow flies through ion gate 1 to ion gate 2. At time t2, ion gate 1 is closed and ion gate 2 is closed. Therefore, the ions that pass through ion gate 1 are bunched into a packet of ions. At time t3, ion gate 1 is closed and ion gate 2 is closed resulting in all the bunched ions reaching the vicinity of ion gate 2 and compressing into a tight ion packet. At time t4, ion gate 1 is closed and ion gate 2 is open resulting in the ion packet near ion gate 2 passing through ion gate 2 to a downstream device. The downstream device may be an orthogonal acceleration region of a TOF mass analyzer. Synchronizing the passage of the ion packet's passage through ion gate 2 with the pulse acceleration voltage of an orthogonal acceleration region can enable a pulse acceleration voltage to improve the duty cycle of a TOF mass analyzer, thereby increasing sensitivity.

Figure 17:
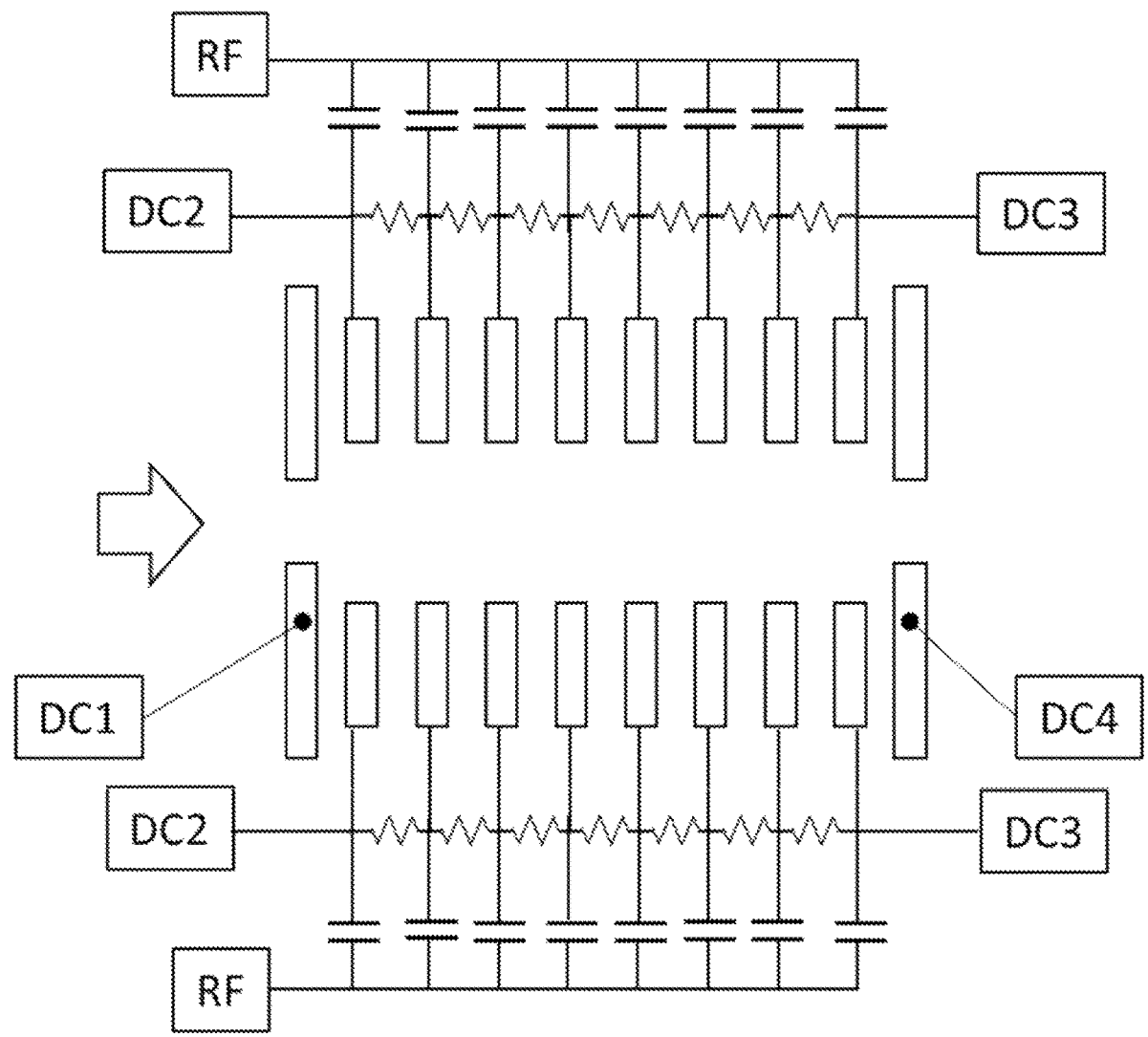
FIG. 17 shows an ion manipulation device based on single RF segmented quadrupole for increasing duty cycle of TOF mass analyzer, in accordance with embodiments of the invention.

FIG. 17 shows a segmented quadrupole with a single RF voltage. The peak-to-peak amplitude of RF voltage may be from 0 volts (V) to 100V, 100V to 200V, 200V to 300V, 300V to 400V, 400V to 500V, 500V to 600V, 600V to 700V, 700V to 800 V, 800V, to 900V, 900V, to 1000V, 1000V to 1100V, 1100V to 1200V, 1200V to 1300V, 1300V to 1400V, 1400V to 1500V, 1500V to 1600V, 1600V to 1700V, 1700V to 1800 V, 1800V3 to 1900V, 1900V to 2000V, 2000V to 2100V, 2100V to 2200V, 2200V to 2300V, 2300V to 2400V, 2400V to 2500V, 2500V to 2600V, 2600V to 2700V, 2700V to 2800 V, 2800V to 2900V, 2900V to 3000V, 3000V to 3100V, 3100V to 3200V, 3200V to 3300V, 3300V to 3400V, 3400V to 3500V, 3500V to 3600V, 3600V to 3700V, 3700V to 3800 V, 3800V to 3900V, 3900V to 4000V, 4000V to 4100V, 4100V to 4200V, 4200V to 4300V, 4300V to 4400V, 4400V to 4500V, 4500V to 4600V, 4600V to 4700V, 4700V to 4800 V, 4800V to 4900V, 4900V to 5000V. The peak-to-peak amplitude of RF voltage may be greater than about 0V, 100V, 200V, 300V, 400V, 500V, 600V, 700V, 800 V, 800V, 900V, 1000V, 1100V, 1200V, 1300V, 1400V, 1500V, 1600V, 1700V, 1800 V, 1900V, 2000V, 2100V, 2200V, 2300V, 2400V, 2500V, 2600V, 2700V, 2800 V, 2900V, 3000V, 3100V, 3200V, 3300V, 3400V, 3500V, 3600V, 3700V, 3800 V, 3900V, 4000V, 4100V, 4200V, 4300V, 4400V, 4500V, 4600V, 4700V, 4800 V, 4900V, or 5000V. The peak-to-peak amplitude of RF voltage may be less than about 5000V, 4900V, 4800V, 4700V, 4600V, 4500V, 4400V, 4300V, 4200V, 4100V, 4000V, 3900V, 3800V, 3700V, 3600V, 3500V, 3400V, 3300V, 3200V, 3100V, 3000V, 2900V, 2800V, 2700V, 2600V, 2500V, 2400V, 2300V, 2200V, 2100V, 2000V, 1900V, 1800V, 1700V, 1600V, 1500V, 1400V, 1300V, 1200V, 1100V, 1000V, 900V, 800V, 700V, 600V, 500V, 400V, 300V, 200V, 100V, or 10V. The peak-to-peak amplitude of RF voltage may be between any values provided above.

The frequency of RF voltage may be from 100 kilohertz (kHz) to 1 megahertz (MHz), 1 MHz to 2 MHz, 2 MHz to 3 MHz, 3 MHz to 4 MHz, 4 MHz to 5 MHz, 5 MHz to 6 MHz, 6 MHz to 7 MHz, 7 MHz to 8 MHz, 8 MHz to 9 MHz, 9 MHz to 10 MHz, 10 MHz to 11 MHz, 11 MHz to 12 MHz, 12 MHz to 13 MHz, 13 MHz to 14 MHz, 14 MHz to 15 MHz, 15 MHz to 16 MHz, 16 MHz to 17 MHz, 17 MHz to 18 MHz, 18 MHz to 19 MHz, 19 MHz to 20 MHz, 20 MHz to 21 MHz, 21 MHz to 22 MHz, 22 MHz to 23 MHz, 23 MHz to 24 MHz, 24 MHz to 25 MHz, 25 MHz to 26 MHz, 26 MHz to 27 MHz, 27 MHz to 28 MHz, 28 MHz to 29 MHz, 29 MHz to 30 MHz, 30 MHz to 31 MHz, 31 MHz to 32 MHz, 32 MHz to 33 MHz, 33 MHz to 34 MHz, 34 MHz to 35 MHz, 35 MHz to 36 MHz, 36 MHz to 37 MHz, 37 MHz to 38 MHz, 38 MHz to 39 MHz, 39 MHz to 40 MHz, 40 MHz to 41 MHz, 41 MHz to 42 MHz, 42 MHz to 43 MHz, 43 MHz to 44 MHz, 44 MHz to 45 MHz, 45 MHz to 46 MHz, 46 MHz to 47 MHz, 47 MHz to 48 MHz, 48 MHz to 49 MHz, 49 MHz to 50 MHz. The frequency of RF voltage may be greater than about 100 kilohertz (kHz), 1 megahertz (MHz), 2 MHz, 3 MHz, 4 MHz, 5 MHz, 6 MHz, 7 MHz, 8 MHz, 9 MHz, 10 MHz, 11 MHz, 12 MHz, 13 MHz, 14 MHz, 15 MHz, 16 MHz, 17 MHz, 18 MHz, 19 MHz, 20 MHz, 21 MHz, 22 MHz, 23 MHz, 24 MHz, 25 MHz, 26 MHz, 27 MHz, 28 MHz, 29 MHz, 30 MHz, 31 MHz, 32 MHz, 33 MHz, 34 MHz, 35 MHz, 36 MHz, 37 MHz, 38 MHz, 39 MHz, 40 MHz, 41 MHz, 42 MHz, 43 MHz, 44 MHz, 45 MHz, 46 MHz, 47 MHz, 48 MHz, 49 MHz, or 50 MHz. The frequency of RF voltage may be less than about 50 MHz, 49 MHz, 48 MHz, 47 MHz, 46 MHz, 45 MHz, 44 MHz, 43 MHz, 42 MHz, 41 MHz, 40 MHz, 39 MHz, 38 MHz, 37 MHz, 36 MHz, 35 MHz, 34 MHz, 33 MHz, 32 MHz, 31 MHz, 30 MHz, 29 MHz, 28 MHz, 27 MHz, 26 MHz, 25 MHz, 24 MHz, 23 MHz, 22 MHz, 21 MHz, 20 MHz, 19 MHz, 18 MHz, 17 MHz, 16 MHz, 15 MHz, 14 MHz, 13 MHz, 12 MHz, 11 MHz, 10 MHz, 9 MHz, 8 MHz, 7 MHz, 6 MHz, 5 MHz, 4 MHz, 3 MHz, 2 MHz, 1 MHz, or 100 kHz. The frequency of RF voltage may be between any values provided above.

A plurality of DC voltages is separately applied to all rod electrodes of each segment to form a DC potential gradient in the axial direction for controlling the flight time of ions. The advantage of the device is that the time required for ions to fly from the ion gate 1 to the ion gate 2 at time t3 can be flexibly controlled to match the time interval between the openings of the two ion gates. This can improve axial ion compression.

Figure 18:
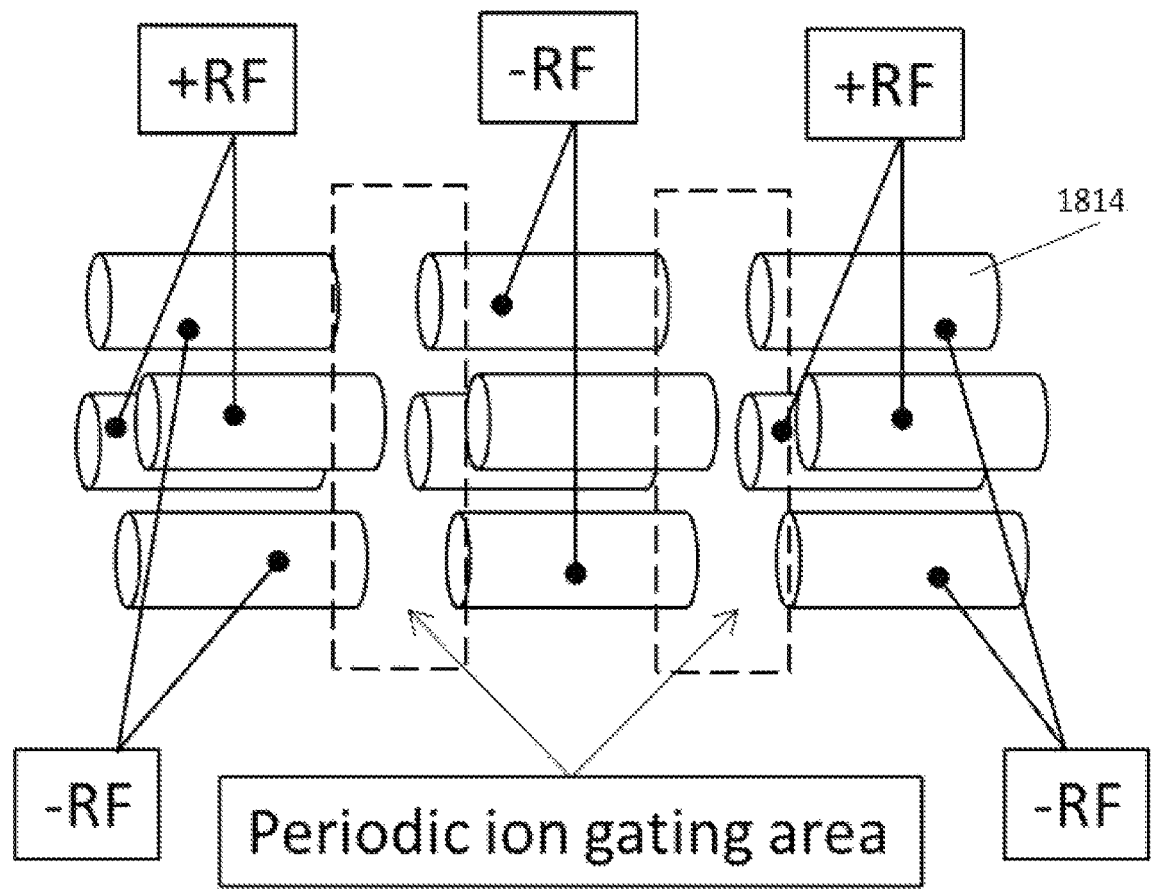
FIG. 18 shows an ion manipulation device based on single RF quadrupole and two short RF quadrupole for increasing duty cycle of TOF mass analyzer, in accordance with embodiments of the invention.

FIG. 18 shows a segmented quadrupole wherein the endcap electrodes disclosed above are replaced with two shortened RF quadrupoles. In this embodiment, ions can be stored in the shortened quadrupole before ion gate 1 between time t2 and t4 to further improve the sensitivity. Alternatively, the shortened quadrupole can be replaced with other devices for ion storage including but not limited to a multipole device, ion tunnel, or ion funnel.

Figure 19:
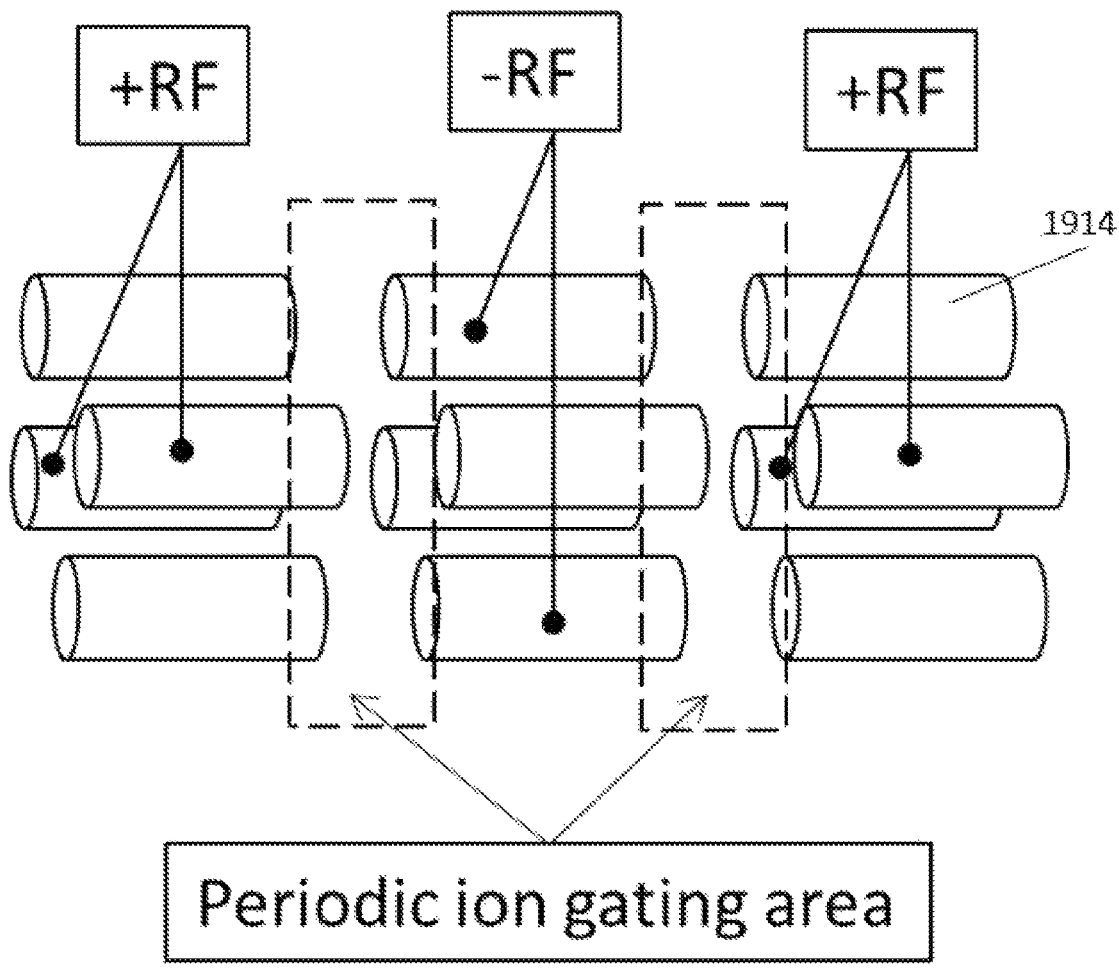
FIG. 19 shows an ion manipulation device based on three single RF quadrupoles for increasing duty cycle of TOF mass analyzer, in accordance with embodiments of the invention.

FIG. 19 shows an ion manipulation device composed of three single RF quadrupole devices. The polarity of single RF voltage applied on adjacent quadrupole component is different. At the same time, the single RF voltages are applied on different rod pairs of adjacent quadrupole components. This configuration may allow for increased sensitivity and control of ion flight time by controlling the movement of ions through the gating areas.

It should be noted that application of the provided methods and systems are not limited by the underlying computing infrastructure or computing environment. For instance, the provided control system may be applied to grid computing platform or systems utilizing various technologies such as mesh computing, peer-to-peer computing, autonomic (self-healing) computing, wireless sensor networks, mobile data acquisition, mobile signature analysis, cooperative distributed peer-to-peer ad hoc networking and processing, local cloud/fog computing and grid/mesh computing, dew computing, mobile edge computing, cloudlet, distributed data storage and retrieval, remote cloud services, augmented reality and the like. It is understood in advance that although this specification includes description of cloud computing, implementation of the teachings recited herein are not limited to a cloud computing environment. Rather, embodiments of the present invention are capable of being implemented in conjunction with any other types of computing environment now known or later developed.

Figure 20:
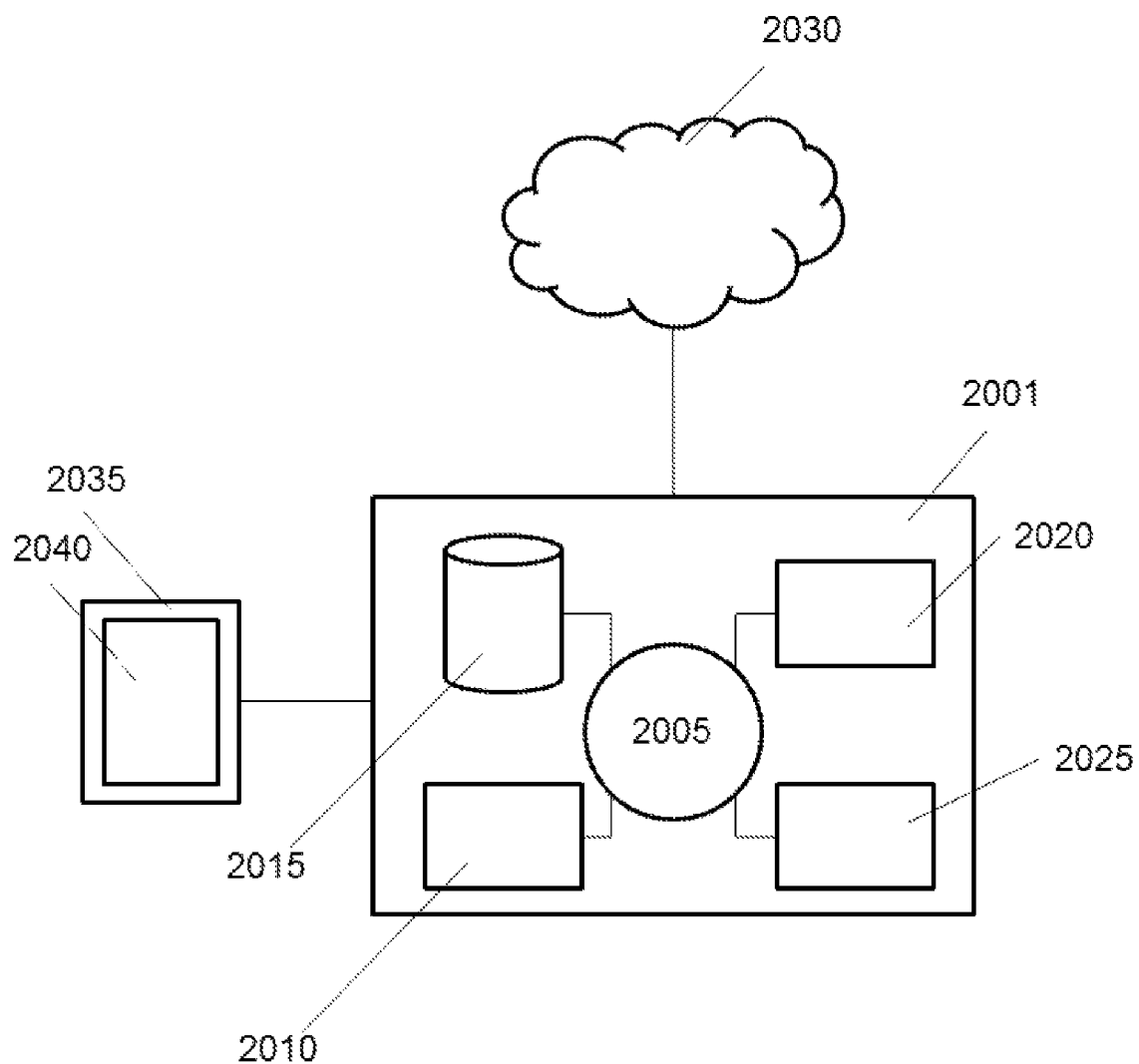
FIG. 20 shows an example of a computer system, provide din accordance with embodiments of the invention.

The present disclosure provides computer systems that are programmed to implement methods and systems of the disclosure. FIG. 20 shows a computer system 2001 that is programmed or otherwise configured to implement a signal processing device as described above. The computer system 2001 can regulate various aspects of the present disclosure, such as, for example, controlling ion gating components and rendering graphical user interfaces and the other functions as described elsewhere herein. The computer system 2001 can be an electronic device of a user or a computer system that is remotely located with respect to the electronic device. The electronic device can optionally be a mobile electronic device.

The computer system 2001 includes a central processing unit (CPU, also "processor" and "computer processor" herein) 2005, which can be a single core or multi core processor, or a plurality of processors for parallel processing. The computer system 2001 also includes memory or memory location 2010 (e.g., random-access memory, read-only memory, flash memory), electronic storage unit 2015 (e.g., hard disk), communication interface 2020 (e.g., network adapter) for communicating with one or more other systems, and peripheral devices 2025, such as cache, other memory, data storage and/or electronic display adapters. The memory 2010, storage unit 2015, interface 2020 and peripheral devices 2025 are in communication with the CPU 2005 through a communication bus (solid lines), such as a motherboard. The storage unit 2015 can be a data storage unit (or data repository) for storing data. The computer system 2001 can be operatively coupled to a computer network ("network") 2030 with the aid of the communication interface 2020. The network 2030 can be the Internet, an internet and/or extranet, or an intranet and/or extranet that is in communication with the Internet.

The network 2030 in some cases is a telecommunication and/or data network. The network 2030 can include one or more computer servers, which can enable distributed computing, such as cloud computing. For example, one or more computer servers may enable cloud computing over the network 2030 ("the cloud") to perform various aspects of analysis, calculation, and generation of the present disclosure, such as, for example, capturing a configuration of one or more experimental environments; performing usage analyses of products (e.g., applications); and providing outputs of statistics of projects. Such cloud computing may be provided by cloud computing platforms such as, for example, Amazon Web Services (AWS), Microsoft Azure, Google Cloud Platform, and IBM cloud. The network 2030, in some cases with the aid of the computer system 2001, can implement a peer-to-peer network, which may enable devices coupled to the computer system 2001 to behave as a client or a server.

The CPU 2005 can execute a sequence of machine-readable instructions, which can be embodied in a program or software. The instructions may be stored in a memory location, such as the memory 2010. The instructions can be directed to the CPU 2005, which can subsequently program or otherwise configure the CPU 2005 to implement methods of the present disclosure. Examples of operations performed by the CPU 2005 can include fetch, decode, execute, and writeback.

The CPU 2005 can be part of a circuit, such as an integrated circuit. One or more other components of the system 2001 can be included in the circuit. In some cases, the circuit is an application specific integrated circuit (ASIC).

The storage unit 2015 can store files, such as drivers, libraries and saved programs. The storage unit 2015 can store user data, e.g., user preferences and user programs. The computer system 2001 in some cases can include one or more additional data storage units that are external to the computer system 2001, such as located on a remote server that is in communication with the computer system 2001 through an intranet or the Internet.

The computer system 2001 can communicate with one or more remote computer systems through the network 2030. For instance, the computer system 2001 can communicate with a remote computer system of a user (e.g., a user of an experimental environment). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2001 via the network 2030.

Methods as described herein can be implemented by way of machine (e.g., computer processor) executable code stored on an electronic storage location of the computer system 2001, such as, for example, on the memory 2010 or electronic storage unit 2015. The machine executable or machine readable code can be provided in the form of software. During use, the code can be executed by the processor 2005. In some cases, the code can be retrieved from the storage unit 2015 and stored on the memory 2010 for ready access by the processor 2005. In some situations, the electronic storage unit 2015 can be precluded, and machine-executable instructions are stored on memory 2010.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 2001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2001 can include or be in communication with an electronic display 1235 that comprises a user interface (UI) 2040 for providing, for example, the various components (e.g., lab, launch pad, control center, knowledge center, etc) of the model management system. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 2005. The algorithm can, for example, generate instructions to operate one or more component of a sample transport system.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. An inductively-coupled plasma time-of-flight mass spectrometer for analysis of single particles tagged with metal isotopes, said mass spectrometer comprising:
   a sample introduction device configured to sequentially generate the single particles;
   an ionization device for generating ions of the metal isotopes from the single particles received through the sample introduction device;
   an atmospheric pressure interface for transport of the ions with aid of a vacuum;
   an ion guide arrangement configured to receive the ions from the atmospheric pressure interface and transport the ions;
   an ion manipulation device configured to receive the ions from the ion guide arrangement and configured to perform one or more of (1) selectively filtering ions with specific masses, (2) providing ion bunching, and (3) providing ion storage;
   a time-of flight (TOF) mass analyzer configured to receive the ions and separate ions with different masses to arrive at an ion detector at different times; and
   a signal processing device configured to process an ion flow signal from the ion detector and form a mass spectrum for identification of the metal isotopes,
   wherein the ion guide arrangement has a curved shape, and
   wherein the ion guide arrangement comprises a first curved electrode having a concave surface, wherein said concave surface comprises a first planar surface and a second planar surface that meets the first planar surface and is not parallel to the first planar surface; a second curved electrode having a convex surface, wherein said convex surface comprises a third planar surface and a fourth planar surface that meets the third planar surface and is not parallel to the third planar surface; and a gap between the first curved electrode and the second curved electrode configured to permit passage of targeted ions between the first curved electrode and the second curved electrode.

2. The mass spectrometer of claim 1, wherein the ion guide arrangement is an electrostatic lens.

3. The mass spectrometer of claim 1, wherein the ion guide arrangement is a quadrupole arrangement.

4. The mass spectrometer of claim 1, wherein the ion guide arrangement is a multipole arrangement.

5. The mass spectrometer of claim 1, wherein the ion guide arrangement is an ion tunnel.

6. A method for analyzing single particles tagged with metal isotopes via an inductively-coupled plasma time-of-flight mass spectrometer, said method comprising:
   sequentially generating the single particles via a sample introduction device;
   generating, with aid of an ionization device, ions of the metal isotopes from the single particles received through the sample introduction device;
   transporting, using an atmospheric pressure interface, the ions with aid of a vacuum;
   receiving, via an ion guide arrangement, the ions from the atmospheric pressure interface, and transporting the ions;
   receiving, via an ion manipulation device, the ions from the ion guide arrangement, and performing one or more of (1) selectively filtering ions with specific masses, (2) providing ion bunching, and (3) providing ion storage;
   separating, via a time-of flight (TOF) mass analyzer, the ions with different masses to arrive at an ion detector at different times; and
   processing, via a signal processing device, an ion flow signal from the ion detector and form a mass spectrum for identification of the metal isotopes,
   wherein the ion guide arrangement has a curved shape, and
   wherein the ion guide arrangement comprises a first curved electrode having a concave surface, wherein said concave surface comprises a first planar surface and a second planar surface that meets the first planar surface and is not parallel to the first planar surface; a second curved electrode having a convex surface, wherein said convex surface comprises a third planar surface and a fourth planar surface that meets the third planar surface and is not parallel to the fourth third planar surface; and a gap between the first curved electrode and the second curved electrode configured to permit passage of targeted ions between the first curved electrode and the second curved electrode.

7. The method of claim 6, wherein the single particles are single cells.

8. The method of claim 6, wherein the sample introduction device is configured to sequentially generate the single particles tagged with metal isotopes.

9. The method of claim 6, wherein the ionization device is an inductively coupled plasma (ICP) ionization device.

10. The method of claim 9, wherein the ionization device is configured to evaporate, atomize, and ionize the single particles.

11. The method of claim 6, wherein the atmospheric pressure interface comprises two or more cone shaped components.

12. The method of claim 6, wherein the atmospheric pressure interface comprises one or more adjacent vacuum chambers.

13. The method of claim 6, wherein the ion guide arrangement utilizes a quadrupole arrangement.

14. The method of claim 6, wherein the ion guide arrangement utilizes a multipole arrangement.

15. The method of claim 6, wherein the ion guide arrangement utilizes an ion tunnel.

16. The method of claim 6, wherein the ion guide arrangement utilizes an ion funnel.

* * * * *